US007668667B2

(12) United States Patent
Robb et al.

(10) Patent No.: US 7,668,667 B2
(45) Date of Patent: Feb. 23, 2010

(54) MINIATURE STIMULATING AND SENSING SYSTEM

(75) Inventors: John Chamberlain Robb, Newburyport, MA (US); Steven W. Arms, Williston, VT (US); Christopher P. Townsend, Shelburne, VT (US); David L. Churchill, Burlington, VT (US); Michael J. Hamel, Essex Junction, VT (US)

(73) Assignee: MicroStrain, Inc., Williston, VT (US)

( * ) Notice: Subject to any disclaimer, the term of this patent is extended or adjusted under 35 U.S.C. 154(b) by 52 days.

(21) Appl. No.: 11/368,731

(22) Filed: Mar. 6, 2006

(65) Prior Publication Data
US 2009/0322557 A1 Dec. 31, 2009

Related U.S. Application Data

(60) Provisional application No. 60/659,338, filed on Mar. 7, 2005.

(51) Int. Cl.
*G01B 5/30* (2006.01)
*G01D 3/00* (2006.01)
(52) U.S. Cl. .................. 702/35; 702/110; 702/111; 702/112; 714/22
(58) Field of Classification Search ............ 702/33–35, 702/110–112; 340/870.16, 505, 10.1, 10.5, 340/572.4, 573.1; 324/664, 666, 690, 693, 324/698, 649; 73/866, 204.17; 137/1; 306/118, 306/776.5; 714/22; 310/339
See application file for complete search history.

(56) References Cited

U.S. PATENT DOCUMENTS 4,288,742 A 9/1981 Walsh
5,260,666 A 11/1993 Dishman
5,338,432 A 8/1994 Agarwala
5,441,527 A 8/1995 Erickson
5,445,178 A 8/1995 Feuer
5,479,104 A 12/1995 Cambell
5,738,107 A 4/1998 Martinsen
5,754,122 A 5/1998 Li
5,859,537 A 1/1999 Davis
6,301,967 B1 10/2001 Donskoy
6,328,878 B1 12/2001 Davis
6,337,994 B1 1/2002 Stoianovici
6,477,907 B1 11/2002 Chambers
6,529,127 B2 3/2003 Townsend
6,807,444 B2 10/2004 Tu (Continued)

OTHER PUBLICATIONS

National Physical Laboratory paper, "Good Practice Guide to Cure Monitoring", "Dielectric Measurements".*

(Continued)

*Primary Examiner*—Edward Raymond
*Assistant Examiner*—Phuong Huynh
(74) *Attorney, Agent, or Firm*—James Marc Leas

(57) ABSTRACT

An electronic system for testing a material includes at least one module for mechanically mounting on the material. The module includes a signal generator for generating a signal generator signal. The module also includes a stimulus signal delivering device (SSDD) and an SSDD circuit for providing a device signal derived from said signal generator signal to the material. The module also includes a sensor and a sensor circuit for receiving an interaction signal derived from interaction of the device signal with the material.

77 Claims, 23 Drawing Sheets

U.S. PATENT DOCUMENTS

| | | | |
|---|---|---|---|
| 6,813,515 | B2 | 11/2004 | Hashimshony |
| 6,819,121 | B1 | 11/2004 | Hager |
| 6,828,779 | B2 | 12/2004 | Townsend |
| 6,832,111 | B2 | 12/2004 | Tu |
| 6,845,660 | B2 | 1/2005 | Hecht |
| 6,853,203 | B2 | 2/2005 | Beylich |
| 6,854,325 | B2 | 2/2005 | Konzelmann |
| 6,882,879 | B2 | 4/2005 | Rock |
| 6,911,828 | B1 | 6/2005 | Brossia |
| 2001/0007151 | A1* | 7/2001 | Vorenkamp et al. ......... 725/151 |
| 2002/0024450 | A1 | 2/2002 | Townsend |
| 2002/0044468 | A1* | 4/2002 | Goodarzi et al. ............. 363/98 |
| 2003/0222656 | A1 | 12/2003 | Phillips |
| 2004/0078662 | A1* | 4/2004 | Hamel et al. .................. 714/22 |
| 2004/0113790 | A1* | 6/2004 | Hamel et al. ............. 340/572.1 |
| 2005/0017602 | A1 | 1/2005 | Arms |
| 2005/0018858 | A1* | 1/2005 | John ........................... 381/60 |
| 2006/0080048 | A1 | 4/2006 | Kessler |
| 2006/0173284 | A1* | 8/2006 | Ackerman et al. .......... 600/422 |

OTHER PUBLICATIONS

Gyuhae Park, Overview of Piezoelectric Impedance-Based Health Monitoring and Path Forward, The Shock and Vibration Digest, vol. 35 No. 6, Nov. 2003 451-463, Sage Publications.

Abbas Fahr, et al Review of IAR NDI Research in support of Ageing Aircraft, NDT.net—Jan. 1999, vol. 4 No. 1.

Charles H. Keilers, et al Damage Detection and Diagnosis of Composites Using Built-in Piezoceramics, SPIE vol. 1917 Smart Structures and Intelligent Systems (1993) 1009.

Seth S. Kessler, et al, Structural Health Monitoring in Composite Materials Using Frequency Response Methods, Nondestructive Evaluation of Materials and Composites V, George Y Baaklini et al editors, Proceedings of SPIE vol. 4336 (2001).

Seth S. Kessler et al, Design of a piezoelectric-based structural health monitoring system for damage detection in composite materials, Smart Structures and Materials 2002, Smart Structures and Integrated Systems, L. Porter Davis, Editor, Proceedings of SPIE vol. 4701 (2002).

Seth S. Kessler et al, Optimization of Lamb Wave Actuating and Sensing Materials for Health Monitoring of Composite Structures, Smart Structures and Materials 2003, Smart Structures and Integrated Systems, Amr M. Baz, Editor, Proceedings of SPIE vol. 5056 (2003).

Seth S. Kessler et al, Packaging of Structural Health Monitoring Components, Smart Structures and Materials 2004: Sensors and Smart Structures Technologies for Civil, Mechanical, and Aerospace Systems, Shih-Chi Liu, Editor, Proceedings of SPIE vol. 5391 (2004).

Nondestructive Evaluation and its New Role, http://www.ndt.net/abstract/wendt96/vol14.htm.

Analog Devices specification, AD5934.

Sabrin Khaled Gebarin, et al, Determining Proper Oil and Filter Change Intervals: Can Onboard Automotive Sensors Help?, Practicing Oil Analysis Magazine, Jan. 2004.

John Degaspari, Recording Oil's Vital Signs, ME Magazine, May 1999, The American Society of Mechanical Engineers.

Electrochemical Impedance Spectroscopy, Solartron, 1999, Allentown, PA.

Solutions for materials characterization, Solartron, brochure, Allentown, PA.

Acellent technologies, Smart Layer, www.acellent.com/products_layer.htrr.

NPL: Good Practice Guid to Cure Monitoring, www.npl.co.uk/materials/cure/gpg/overview_dielectric.html.

Acellent technologies, Smart Suitcase, www.acellent.com/products_suitcase.htm.

Digital Synthesis, http://arts.ucsc.edu/ems/music/equipment/synthesizers/digital/digisy. ...

Seth S. Kessler, Wireless Nodes for Active Structural Monitoring in Extreme Environments, Presented at the AFRL Integrated Systems Health Management Conference Aug. 17, 2004 http://web.mit.edu/sskess/www/ppt/AFRL04.pdf.

Seth S. Kessler, "Validation of a Lamb Wave-Based Structural Health Monitoring System for Aircraft Applications." Presented at the SPIE Symposium on Smart Structures and Materials, Mar. 8, 2005, http://web.mit.edu/sskess/www/ppt/SPIE05.pdf.

* cited by examiner

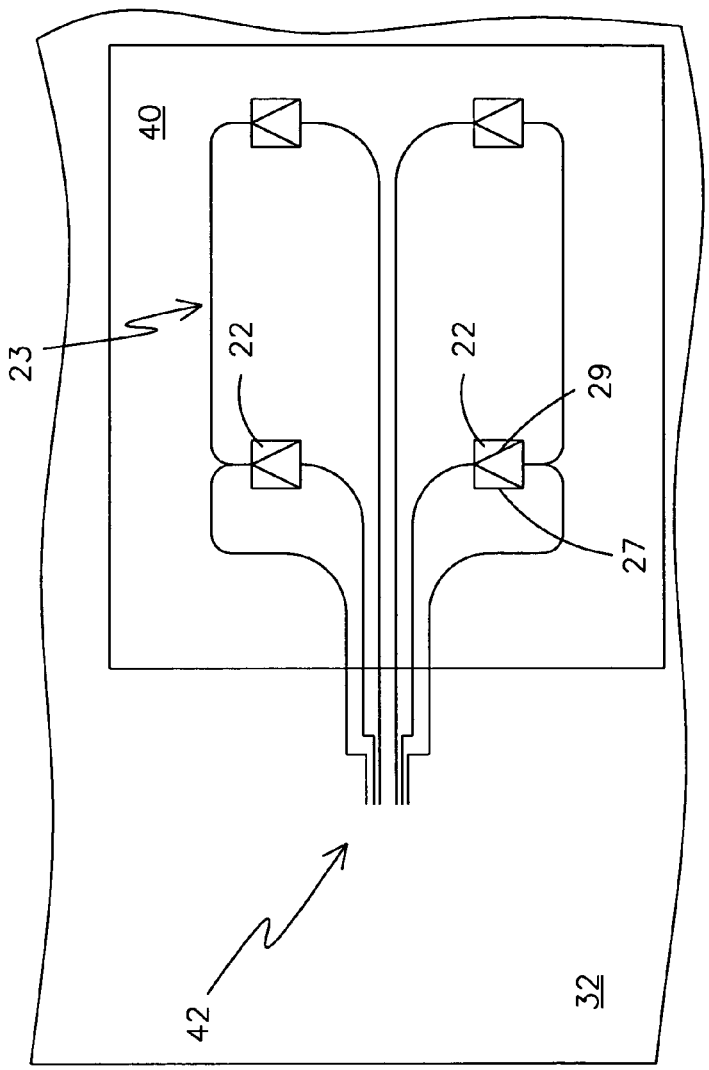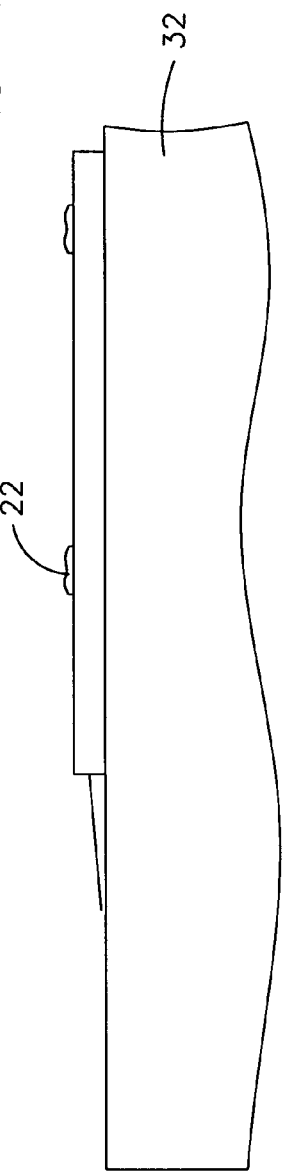
FIG. 1a PRIOR ART
FIG. 1b PRIOR ART

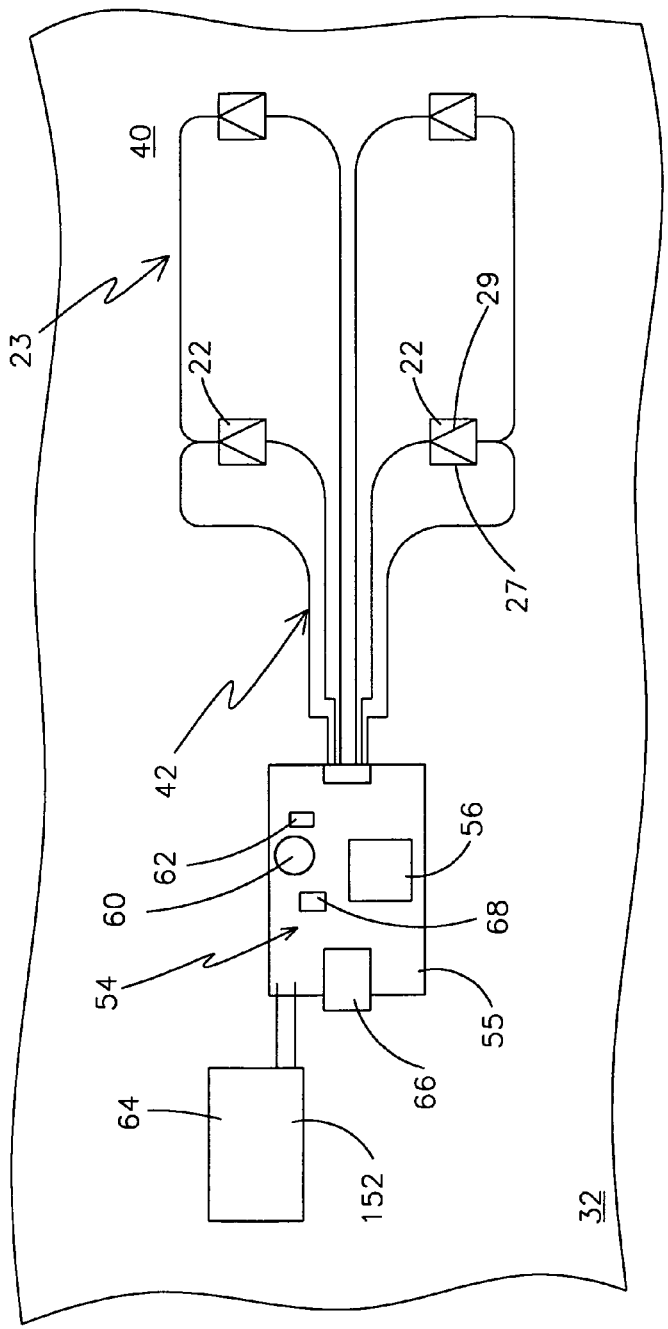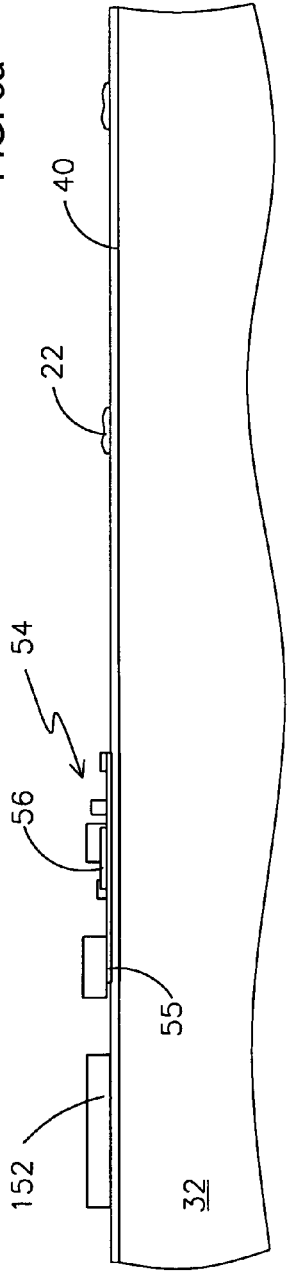
FIG. 3a
FIG. 3b

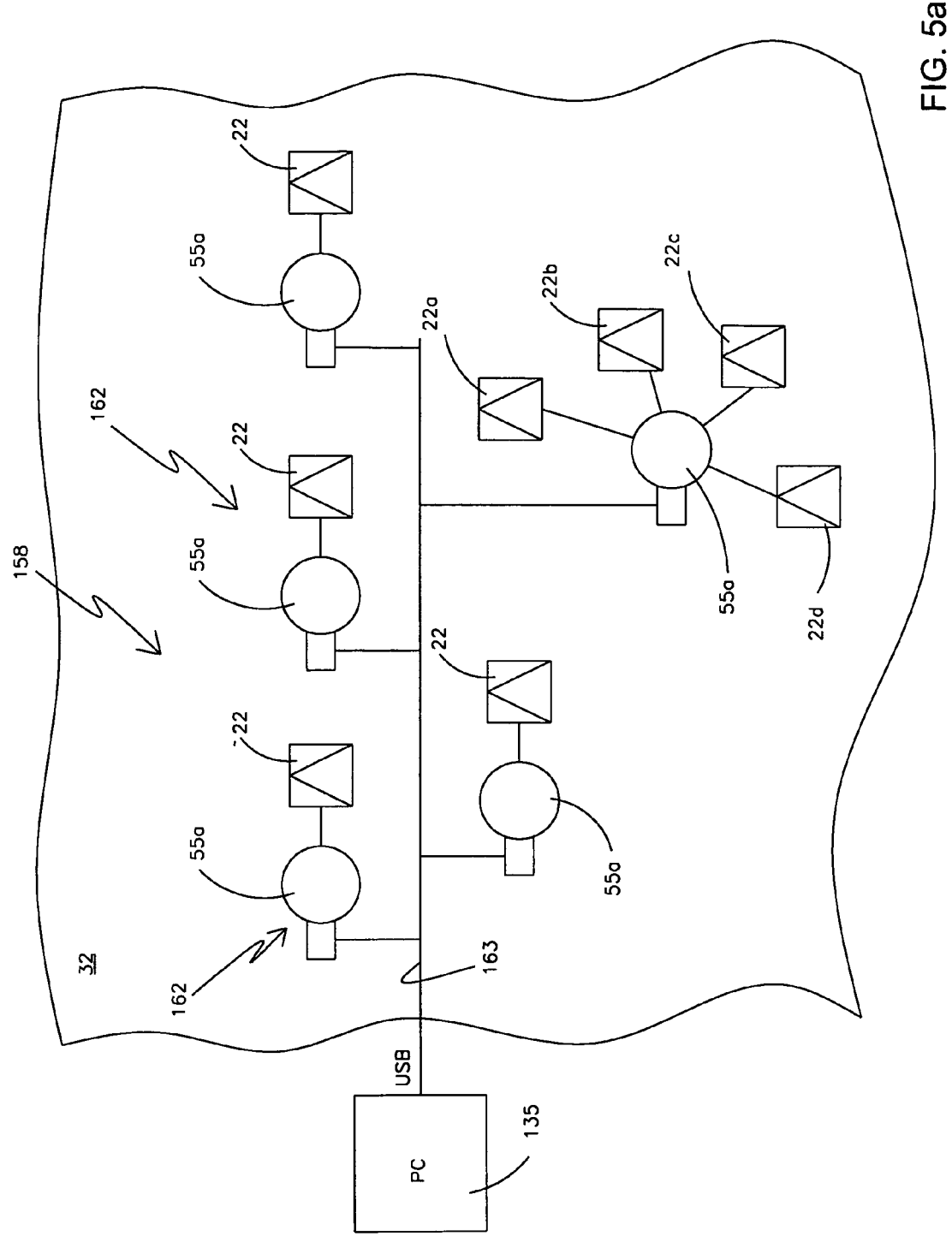

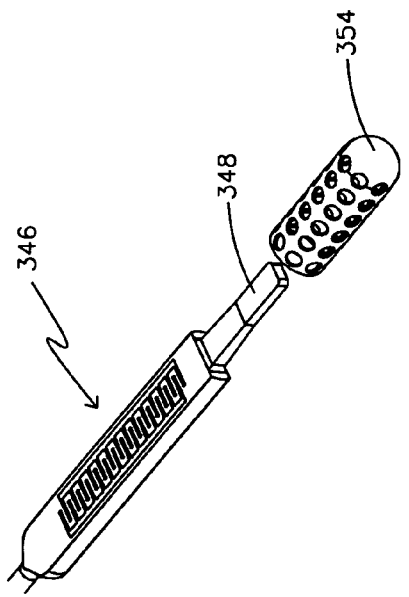
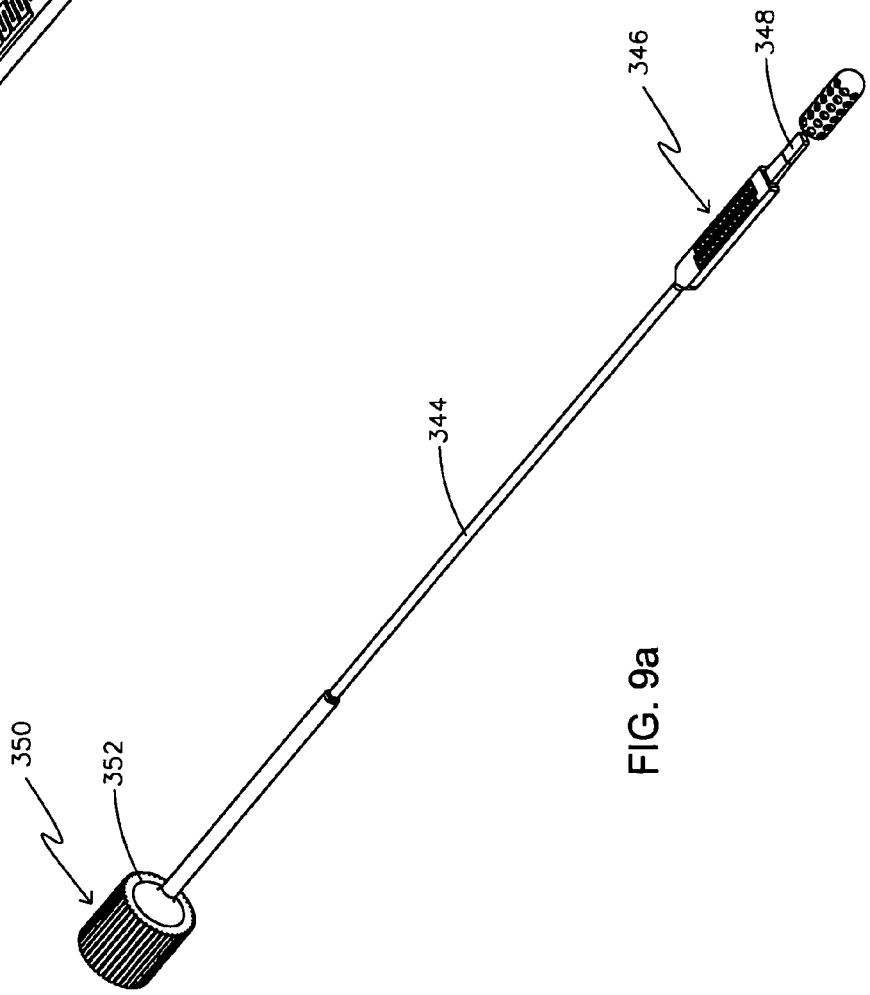

MINIATURE STIMULATING AND SENSING SYSTEM

RELATED APPLICATION AND PRIORITY

This application claims priority of Provisional U.S. Patent Application 60/659,338, filed Mar. 7, 2005, incorporated herein by reference.

This application is related to commonly assigned U.S. Pat. No. 6,529,127, "System for Remote Powering," issued Mar. 4, 2003, incorporated herein by reference.

This application is related to the following commonly assigned U.S. Patent Applications, all of which are incorporated herein by reference:

Ser. No. 09/731,066, "Data collection and Storage Device," filed Dec. 6, 2000,

Ser. No. 10/379,223, "Energy Harvesting for Wireless Sensor Operation and Data Transmission," filed Mar. 5, 2003, Ser. No. 10/769,642, "Shaft Mounted Energy Harvesting for Wireless Sensor Operation and Data Transmission," filed Jan. 31, 2004,

FIELD

This patent application generally relates to sensors. More particularly, it relates to a system for providing a stimulation to a material and sensing a response.

BACKGROUND

Acoustic monitoring systems and other stimulating and sensing electronic devices may be located on substrates, such as aircraft and other vehicles, bridges, buildings, machinery, pipelines, and other structures, to check for cracks, de-lamination, corrosion, or other degradation or damage. Many papers have been published showing these devices.

Lamb waves have long been used for nondestructive test, and a review article, "Review of IAR NDI Research in support of Ageing Aircraft," incorporated herein by reference, by Fahr, Komorowski, Forsyth, Chapman, NDT.net—January 1999, Vol. 4 No. 1, and available at http://www.ndt/article/padndt98/12/12.htm, cites many references. The article provides a review of nondestructive test, including several ways of using the acoustic waves generated with piezoelectric transducers to test materials. The paper also sites research papers describing fatigue mechanisms of aging aircraft that can be tested with lamb waves to find such defects as corrosion, delamination, and cracks. The paper describes several ways of coupling piezoelectric transducers to the material under test but includes no description of the source of stimulation or data analysis. An extensive wiring harness between the piezoelectric transducers appears to be needed to connect the piezoelectric transducers to racks of electronics that provide the stimulating waveform and that receive and analyze the data.

"Structural Health Monitoring in Composite Materials Using Frequency Response Methods," Kessler, et al, *Nondestructive Evaluation of Materials and Composites*, Proceedings of SPIE Vol. 4336 (2001), provides a "survey of candidate methods for the detection of damage in composite materials."

"Design of piezoelectric-based structural health monitoring system for damage detection in composite materials," Kessler and Spearing, *Smart Structures and Integrated Systems*, Proceedings of SPIE Vol. 4701 (2002), describes the use of Lamb wave techniques to test specimens containing damage and the use of piezoelectric patches as actuators and sensors.

"Optimization of Lamb Wave Actuating and Sensing Materials for Health Monitoring of Composite Structures, Kessler and Dunn, *Smart Structures and Materials 2003: Smart Structures and Integrated Systems*, Proceedings of SPIE Vol. 5056 (2003), further describes the effectiveness of Lamb wave methods for health monitoring of composite structures and provides results concerning the sensing patch and algorithms for filtering resulting signals.

"Packaging of Structural Health Monitoring Components," Kessler et al., *Smart Structures and Materials 2004: Smart Structures and Integrated Systems*, Proceedings of SPIE Vol. 5391 (2004) further describes "the ability of Lamb waves methods to provide reliable information regarding the presence, location and type of damage in composite specimens." The paper also provides ways to package a wired structural health monitoring device with components for mounting on a substrate to be tested. The package includes leads extending to a function generator and to a data acquisition device. The paper mentions the need for further research to produce a fully functional SHM system that would "include the batteries, wireless communication and local storage device as well as system software."

Such systems have required separate pairs of wires 20, 20' extending from each acoustic actuator/sensor 22 of array 23 of such actuator/sensors to its own rack 24 of large electronic devices, as shown in FIGS. 1a, 1b, and 2. Each rack 24 includes programmable function generator 26 and digital storage oscilloscope 28. At least one computer 30 is also needed, and that computer 30 can serve all the racks 24 of electronic devices and all the actuator/sensors 22. Each programmable function generator 26 provides a desired waveform to the actuator/sensor 22 acting as an actuator 27. Digital storage oscilloscope 28 provides memory for receiving and recording data sensed by those actuator/sensors 22 acting as sensors 29. Computer 30 then receives the data from digital storage oscilloscopes 28 and provides data analysis, as shown in FIG. 2.

One system, available commercially from Acellent, Inc., Sunnyvale, Calif., can be used for analyzing substrate 32 on which it is mounted. The system includes array 23 of actuator/sensors 22 and wiring integrated on insulating film 40 extending to connector 42 to which a wiring harness, including wires 20, 20' for each actuator/sensor, were connected. Wires 20, 20' within this wiring harness could extend to the racks 24 of electronics located off of the substrate, such as schematically illustrated in FIG. 2. Alternatively, the racks of electronics were shrunk to a "smart suitcase," as shown in product literature provided by Acellent available on line at http:/www.acellent.com/products_layer.htm in which 30 sensor/actuators were wired to the smart suitcase. Thus, a wiring harness with 60 wires would be connected from an array of Acellent system actuator/sensors 22 to the electronics located in the smart suitcase. That electronics, including both the signal generation and the data acquisition hardware, was provided in the suitcase, which weighed about 18 pounds.

The need for separate pairs of wires 20, 20' for each actuator sensor 22 and the need for a separate rack 24 of large electronic devices for each actuator/sensor 22 or for a smart suitcase with those electronic devices has limited the number of actuator/sensors 22 that could be provided on a structure, the types of structures that could be monitored, the frequency of monitoring, and the duration of monitoring. The ability to monitor during actual operation of certain structures, such as aircraft wings was also limited.

A source of electrical stimulation has been applied to a material through electrodes or through a device, such as capacitor, that includes a portion of the material. Impedance measurements have been used to provide important information about the material. For example, U.S. Pat. No. 6,911,828 to Brossia et al., provides a system for monitoring the effectiveness of a coating on a substrate surface and indicating the failure of the coating to adequately protect the surface from corrosion, degradation, and the like. The system includes a sensor array positioned in contact with the coating utilizing a number of sensor electrodes connected to a single integrated circuit or a number of separate individual sensor circuits. The electrodes of the sensor array make measurements of the electrochemical impedance characteristics of the coating and provide such data by way of telemetry to a data interrogation device that is periodically be placed in proximity to the sensor array. The interrogation device may serve to both power the sensor array and trigger it to acquire data. A nominal parameter N', which is the product of the impedance magnitude and the phase angle, is utilized as a direct indication of the resistance and capacitance characteristics of the coating and therefore a direct indication of the coatings effectiveness. Variations in the frequency of the interrogation signals transmitted from the data interrogation device signal frequency would permit not only the discreet interrogation of a single sensor at a time but also the acquisition of signal data associated with a variety of sensor frequencies.

A paper, "Overview of Piezoelectric Impedance-Based Health Monitoring and Path Forward," by Gyuhae Park, et al., *The Shock and Vibration Digest*, Vol. 35, No. 6, November 2003, p. 451-463 ("the Park paper"), incorporated herein by reference, describes an approach to piezoelectric impedance-based health monitoring with piezoceramic (PZT) materials.

The impedance based health monitoring system is based on the recognition that "the electrical impedance of the PZT is directly related to the mechanical impedance of the host structure, allowing the monitoring of the host structure's mechanical properties using the measured electrical impedance. Consequently, any changes in the electrical impedance signature can be considered an indication of changes in the structural integrity." In this approach changes in properties of the host structure can be detected simply by monitoring the electrical impedance of the PZT patch over a range of frequencies of the stimulating vibratory signal.

The Park paper describes using "piezoelectric sensors/actuators to acquire dynamic responses of a structure" over the range of frequencies and discusses the relationship between defect size and frequency of signal. The Park paper mentions that the sensors can be used to check the perfection of the bonding of the piezoelectric sensors/actuators to the structure.

The Park paper lists alternate non destructive evaluation techniques, including ultrasonic technology, acoustic emission, magnetic field analysis, penetrant testing, eddy current techniques, X-ray analysis, impact-echo testing, global structural response analysis, and visual inspections. It notes that pulse-echo techniques can be nicely integrated with the impedance method. The Park paper also mentions deploying a network of sensors, in which "each individual PZT patch is activated as an actuator in turn, and the rest of the PZTs act as sensors scanning a large area."

Under a discussion of "future issues," the Park paper states, "the development of standalone, miniaturized impedance measurements system should be pursued." It also notes that the deployment of a dense array of sensors "potentially produces difficulties and complexities in data acquisition and processing. The efficient management of data from a largely distributed sensing system is an important and challenging issue."

The Park paper also notes a "drawback in using multiple sensors is the wiring harnesses needed to connect the sensors to signal processing and computers for obtaining the required information regarding the health of the host systems. Therefore, the integration of wireless telemetry systems into the impedance-measuring unit is imperative to manage and operate the sensing devices."

The Park paper also notes, "recognizing the fact that it takes much more energy to transmit data than to perform the local computation, it is important to embed local processing capabilities at the sensors and use a telemetry system to send only essential data."

The Park paper also states, "another important issue in designing such a system is the management of the power consumption." It recognizes a proposal "to use the voltages generated by natural or ambient vibration in a system. The proposed device is coupled with the PZT, stores the electric energy in a capacitor (or recharges a battery), regenerates it through discharge in a controlled signal for diagnostics and runs the telemetry of the wireless sensing system."

The Park paper states that "a device, which incorporates algorithms in the areas of impedance acquisitions, embedded signal processing, telemetry, and power management mentioned above into one package, will provide significant potential in structural health monitoring and damage prognosis efforts. This device would have a network of sensors in control and can act as a station between sensor networks and the central health monitoring station."

However, such a desired device has not been available for monitoring structures. Nor has a way to make such a device been provided. This description and such a device are provided in the present patent application. In addition, a better scheme is needed to reduce or eliminate the wiring and to reduce or eliminate the racks of large electronic devices, and this scheme is also provided by this patent application.

SUMMARY

One aspect of the present patent application is an electronic system for testing a material. The system includes at least one module for mounting on the material. The generating a signal generator signal. The module also includes a stimulus signal delivering device (SSDD) and an SSDD circuit for providing a device signal derived from said signal generator signal to the material. The module also includes a sensor and a sensor circuit for receiving an interaction signal derived from interaction of the device signal with the material.

Another aspect of the present patent application is a method of operating a structure. The method includes mounting an SSDD and a sensor to a portion of the structure. It also includes mounting a first electronic circuit to that portion for stimulating the SSDD and mounting a second electronic circuit to the structure for receiving information from the sensor. The second electronic circuit includes memory for storing the information from the sensor. While operating the structure in normal operation the method involves using the SSDD and the sensor to determine a property of the portion.

Another aspect of the present patent application is a method of operating a structure. The method includes mounting a signal generator to the structure, the signal generator for generating a signal generator signal. The method also includes mounting a stimulus signal delivering device (SSDD) to the structure for providing a device signal to the structure wherein the device signal is derived from the signal generator signal. It also includes mounting a circuit to the structure for receiving an interaction signal, wherein the interaction signal is derived from interaction of the device signal with the material.

BRIEF DESCRIPTION OF THE DRAWINGS

The foregoing will be apparent from the following detailed description as illustrated in the accompanying drawings, in which:

FIG. 1a is a top view of a prior art array of commercially available piezoelectric transducers integrated into a film that can be mounted on a substrate with wiring for connection to a rack of large electronic devices or to a "smart suitcase" of electronics located off the substrate that provides stimulation to the transducers and that receives and records data sensed by the transducers;

FIG. 1b is a cross sectional view of the prior art array of FIG. 1a

FIG. 3a is a top view of an array of piezoelectric transducers in combination with an embodiment of the miniaturized electronics of the present patent application, shown in detail in FIGS. 4a-4e, in which both transducers and miniaturized electronics are mounted on a substrate;

FIG. 3b is a cross sectional view of the array of transducers and the miniaturized electronics of FIG. 3a;

FIG. 5a is a schematic diagram showing an array of smart actuator/sensors wired together with a USB connector;

FIGS. 9a-9b are three dimensional diagrams of a dip stick for use in an internal combustion engine having miniaturized electronics as shown in FIGS. 4a-4e and 8a-8c in the handle and having impedance measuring and vibration delivering and sensing devices;

DETAILED DESCRIPTION

Figure 2:
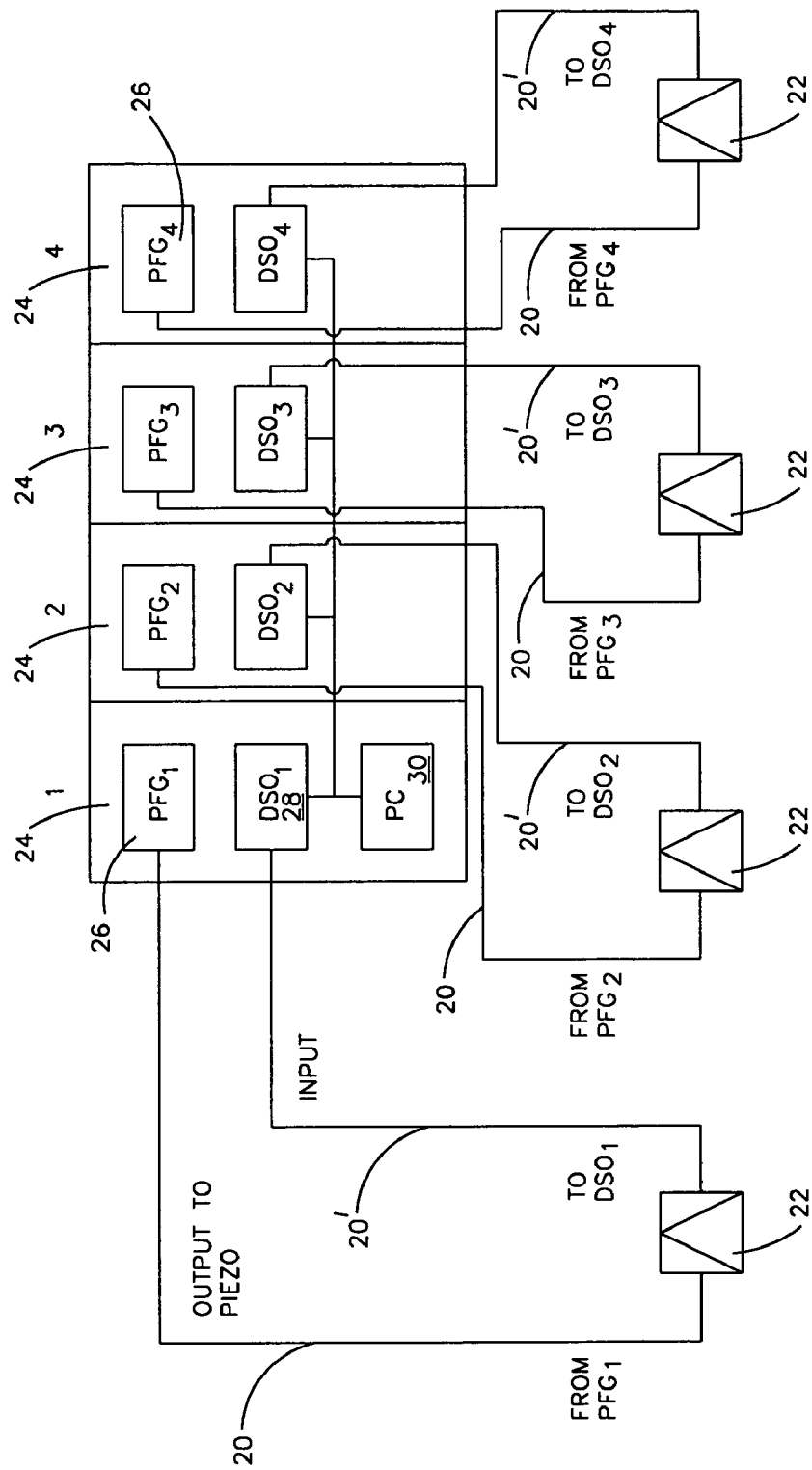
FIG. 2 is a schematic diagram of the prior art array of commercially available piezoelectric transducers integrated into a film, as shown in FIGS. 1a, 1b, racks of electronic devices, and the wiring extending there between for providing stimulation to the array of transducers and for receiving and recording data from the transducers.

The present application provides a miniaturized stimulating and sensing system that can be used for testing a substrate. The system includes a module connected to a separate actuator and sensor or to an integrated actuator/sensor. The actuator is for stimulating the substrate and the sensor is for sensing changes in the substrate detected in a signal derived from that stimulation. The module includes miniaturized electronics for controlling the stimulation to the actuator and for receiving, storing, and analyzing the data collected by the sensor. The system also includes a base station for receiving information from the module and providing instructions or programs to the module. Wiring is reduced by providing the miniaturized electronics inside the module for mounting on the substrate along with the actuator and the sensor. Wiring between module and base station is reduced by providing addressable modules. Wiring may be eliminated by providing a wireless communications link there between.

The substrate can be an aircraft, train, truck, automobile, or other vehicle. It can also be a bridge or a building. It can also be machinery, a pipeline, or any other structure. It can be a composite material, concrete, a metal, or any other type of material. In this application mounting a module "to" a substrate means mounting the module on an exterior or interior surface of the substrate. "To" a substrate also means embedded within the substrate. Thus, a module mounted on an outer surface or on an inner surface of a pipeline is mounted to the pipeline. A module embedded within concrete is considered to be mounted to the concrete for the purposes of this application. A module mounted on a surface of a wing of an aircraft or on any interior member within the wing is considered to be mounted to the wing for the purposes of this application. A module mounted on a beam within a wall is considered to be mounted to the beam and also to the wall.

The actuator and sensor can be distinct devices. Alternatively, a single "actuator/sensor" can both provide a stimulus signal and sense a response to that stimulus. For example a piezoelectric transducer can both provide vibration to a substrate and sense vibration coming from that substrate. In actuator mode the piezoelectric transducer may convert an electrical signal into a vibration that can move from the piezoelectric transducer through any material it contacts, such as a pipeline or the air. In sensing mode the piezoelectric transducer may transform a vibration it senses into an electrical signal that can be amplified, stored in memory, or otherwise processed. The vibration produced by or sensed by the piezoelectric transducer may be considered an acoustic signal regardless of whether the frequency of the vibration is within the range that is detectable by the human ear.

A paper, "Damage Detection and Diagnosis of Composites Using Built-In Piezoceramics," incorporated herein by reference, by Keilers and Chang, SPIE Vol. 1917, *Smart Structures and Intelligent Systems*, 1993, p. 1009-1019, provides a way to determine the location of a crack in a substrate by providing piezo elements on the substrate, some acting as actuators and others as sensors. The paper describes providing wires leading to each piezo element.

Although the need for a standalone, miniaturized piezoelectric impedance measurements system capable of controlling the sensors and actuators of that system wirelessly and with embedded local processing at the sensors were all known as of the November 2003 date of the Park paper, no description of how to accomplish any of this was provided. Such description is provided in the present patent application.

The present application provides the same functions of wave form generation and data acquisition as the rack mounted electronics or the smart suitcase but provides an embodiment of the electronics to perform these functions that is much smaller so that it can be integrated on the substrate along with the actuators and sensors. Thus, long wiring to either racks or to a smart suitcase is avoided.

In one embodiment of the present application, a program to perform diagnostics on the stored data can also be provided that runs on a microprocessor included with the electronics integrated on the substrate. Results of diagnostics performed within the onboard microprocessor can then be wirelessly transmitted to a base station, such as a personal computer. Alternatively, the raw data can be wirelessly transmitted to the personal computer to run the diagnostics.

In one embodiment, programmable wave form generation and data acquisition are provided along with each actuator/sensor. Thus, a user may change the stimulus wave form after the hardware has been installed, even if the hardware has been installed in a restricted access location. This reprogramming may be accomplished over a wired or wireless link, such as over a wired or wireless network.

Thus, the present patent application eliminates the need for either racks of electronics or a smart suitcase of electronics. It also eliminates the wiring harness extending between actuator/sensors and the racks or suitcase.

One embodiment provides miniaturized electronic devices for providing a stimulating wave, actuation, sensing, data logging, control, and data analysis for mounting on a structure. In one embodiment miniaturized electronics 54 is mounted on flex 40 connected to array 23 of actuator/sensors 22, as shown in FIGS. 3a, 3b. In one scheme flex 40 is bonded on substrate 32. Miniaturized electronics 54 can be mounted directly on flex 40 or it can first be mounted on a separate flex or printed circuit board 55 for mounting on flex 40.

The present inventors built miniaturized electronics 54 on printed circuit board 55 for connection to an individual actuator and an individual sensor. Board 55 and miniaturized electronics 54 mounted thereon had a volume equal to or less than ¼ cubic inch. Board 55 had an active two sided area equal to or less than about 2 square inches, about equal to the area of a US quarter dollar.

The drawing in FIG. 3a is not necessarily to scale. Actuator/sensors 22 can be widely separated on a structure while miniaturized electronics 54 may be postage stamp sized.

Miniaturized electronics 54 includes microcontroller 56, which is connected to signal generator circuit 60, sensor input circuit 62, power supply 64, 64a-64d, communications link 66, 66a, 66b, and programmable interface 68, as shown in FIGS. 4a-4d.

Signal generator circuit 60 includes programmable waveform generator 70 and amplifier 72 to provide a programmable stimulation to a stimulus signal delivering device (SSDD) 74, which can be a piezo actuator, as shown in FIGS. 4a-4d. Programmable waveform generator 70 may generate its signal derived from data received through communications link 66a, 66b and stored in storage device 76 on microcontroller 56. Storage device 76 can be a 64K flash memory. Larger onboard nonvolatile memory or external nonvolatile memory can also be used.

Microcontroller 56 can be part of programmable waveform generator 70, as shown in FIGS. 4a-4e. Microcontroller 56 provides a series of voltage levels by means of 12 bit DAC 78. That series of voltage levels forms a wave form shape that is then filtered and amplified. In one embodiment, microcontroller 56, such as a Silicon Laboratories C8051F061 processor, can download a waveform table including a waveform or a plurality of waveforms from a base station through its input/output communications link 66a, 66b. The waveform table may, for example, be a 512 byte waveform table. Microcontroller 56 can be programmed to choose a desired stimulus signal from the plurality of waveforms in memory. Microcontroller 56 can store data for this digitized waveform in a designated area of its flash memory 76 or in a separate memory chip. Alternatively, flash memory 76 can store many different digitized waveform data sets and microcontroller 56 can select from among these digitized data sets.

A paper, "Digital Synthesis," by Peter Elsea, published in 1996, incorporated herein by reference, describes how to use a wave table lookup to create a sound in a frequency generator. The paper describes a well known technique for digital synthesis for generation of a desired sound. The usual application is to make sounds of musical instruments.

The present applicants incorporated this wave table lookup idea to excite a piezoelectric device that is coupled to the substrate to provide a programmable acoustic stimulation signal. The programmable acoustic stimulation signal can include a multitude of frequencies.

When stimulation is to be provided, this waveform table data is read from flash memory 76 by microprocessor core 80 within microcontroller 56 one byte at a time and put out through 12 bit DAC 78 at a rate of 370 ns per byte. The resulting synthesized waveform is low pass filtered and amplified by operational amplifier 86, such as Analog Devices AD8033AKS. Together, microcontroller 56 and operational amplifier 86 thus form programmable waveform synthesizer 70. Operational amplifier 86 drives pulse power amplifier 72 comprised of push-pull transistor pair 88, such as a Panasonic XP0465400LCT. Output 89 of pulse power amplifier 72 drives the attached SSDD 74 which may be a piezo actuator element. Negative feedback from output 89 of push pull power amplifier 72 provides one of the inputs to operational amplifier 86 to control gain or signal level at output 89.

SSDD 74 receives the analog signal and in turn provides a stimulus signal to substrate 32, as shown in FIGS. 3a, 3b. Thus, the stimulus signal is derived from the programmable signal generator signal. SSDD 74, such as a piezoelectric transducer, can thus initiate an acoustic signal, such as a vibration, in substrate 32 to which it is mounted.

When SSDD 74 provides the stimulus signal to substrate 32, sensor input circuit 62 is used to receive response data derived from interaction of the stimulus signal with substrate 32, convert that analog response data to digital in A/D converter 92, provide that digital data for recording in random access memory (RAM) 93 or in another memory device, and provide that data for analysis in microprocessor core 80.

The output of sensor 61 is provided along wires 90a and 90b to differential sensor input circuit 62 to reject noise, amplify, and digitize. Circuit 62 includes instrumentation amplifier 95, such as an Analog Devices AD623A, which differentially amplifies the signal from sensor 61 to eliminate noise and to amplify what would ordinarily be a very small signal. Differential amplification involves amplifying the voltage difference between the two electrodes coming from sensor 61. Noise or another signal that is equally present in both wires 90a, 90b is eliminated by taking the difference between the signals on both wires, thus leaving the actual signal provided by sensor 61.

Since the amount of amplification needed is not generally known in advance, a programmable amplifier is desirable, and the programmability allows for varying the amplification provided. Also, providing two stages of amplification provides advantage in keeping the noise down. The gain of instrumentation amplifier 95 is programmed to have a range between 4 and 100 times using addressable programmable digital potentiometer 96, such as Analog Devices AD5162B, the resistance of which has been set under program control via a Serial Peripheral Interface (SPI) bus connection from microcontroller 56.

The output of instrumentation amplifier 95 drives the input of operational amplifier 98, such as Analog Devices AD8029A. Operational amplifier 98 is configured to have programmable gain by controlling it with addressable digital potentiometer 100, such as another Analog Devices AD5162B, in a voltage divider configuration with passive circuit component elements (not shown). The gain of this stage is set by microcontroller 56 under program control via the same SPI bus connection 102 which addresses programmable digital potentiometers 96, 100 separately.

Thus, instrumentation amplifier 95 provides the differential programmable amplification and op amp 98 provides additional programmable amplification, each with their addressable programmable digital potentiometers 96, 100.

In addition, a programmable DC voltage offset bias is selectable by program control and provided from 12 bit DAC 104 through operational amplifier 106, which is used as a buffer, into instrumentation amplifier 95. The voltage offset bias is provided so analog to digital (A/D) converter 92 receives a signal in the range from 0-3 volts, where it performs best, and where no part of the signal from sensor 61 is cut off.

The resulting properly conditioned signal from operational amplifier 98 is presented at 16 bit analog to digital conversion port 92 of microcontroller 56. The signal is digitized by A/D converter 92 at a non-zero rate up to a maximum of 1 million 16 bit samples per second. Each of those digital samples provides a measure of the magnitude of signal from sensor 61 at that point in time, and the more samples per second, the greater the accuracy of the digital representation. From 16 bit A/D converter 92 data is sent directly to random access memory (RAM) 93 by way of direct memory access (DMA) controller 94 for temporary storage. For the C8051F061 microcontroller we used, which only has 4K of RAM, we can only take 2 mS of 16 bit data at this rate. Of course, additional RAM can be provided, either by providing a different microcontroller or by using additional data storage devices. Data storage devices include DRAM, SRAM, and NVRAM chips. The number of samples taken is under control of a program that is running on microprocessor core 80.

Simultaneous with the digital recording of data from sensor 61 in RAM 93 is the digital recording of the loaded synthesized waveform as it has been divided down by means of passive resistor voltage divider 110 and presented to 16 bit A/D 112 on microcontroller 56 from which it is sent to RAM 93 by DMA controller 94. This allows identifying, correlating, and comparing the sensor signal detected in A/D converter 92 with the actuator drive pulse, as received in A/D converter 112. Thus, a way to monitor the apparatus itself is provided to determine that the actuator drive pulse was good and that sensor 61 was receiving the expected signal in response. Thus, a cracked or defective piezo actuator or a defective bond between actuator and substrate can be found. A comparison can also be made between the loaded synthesized wave form as received by A/D converter 112 with the stored waveform provided from flash memory 76 within microcontroller 56 to ensure that the signal provided is the one desired. Either way one can detect a cracked or defective SSDD 74 or a degraded bond of SSDD 74 with substrate 32 because the loaded waveform will not be as expected if SSDD 74 is defective or the bond with substrate 32 is degraded.

Time delay can also be used to provide information about the health or the condition of the material under investigation as signal propagation time gives information about its mechanical properties.

The sample rate of A/D converter 92 and A/D converter 112 can be as high as 1 megasample per second and the sample rates and the duration of sampling may be programmed over communications link 66a, 66b and stored in flash memory 76. The timing of the A/D conversions is precisely maintained by microcontroller 56 system clock which is controlled by a crystal oscillator vibrating at 33 Mhz (not shown).

A program for analyzing the digital data to determine a property of the material from the data received can be stored in flash memory 76 and run in microprocessor core 80. Microprocessor core 80 can also include a program providing parameters for the analysis, such as the frequency of sampling data.

Figure 4A:
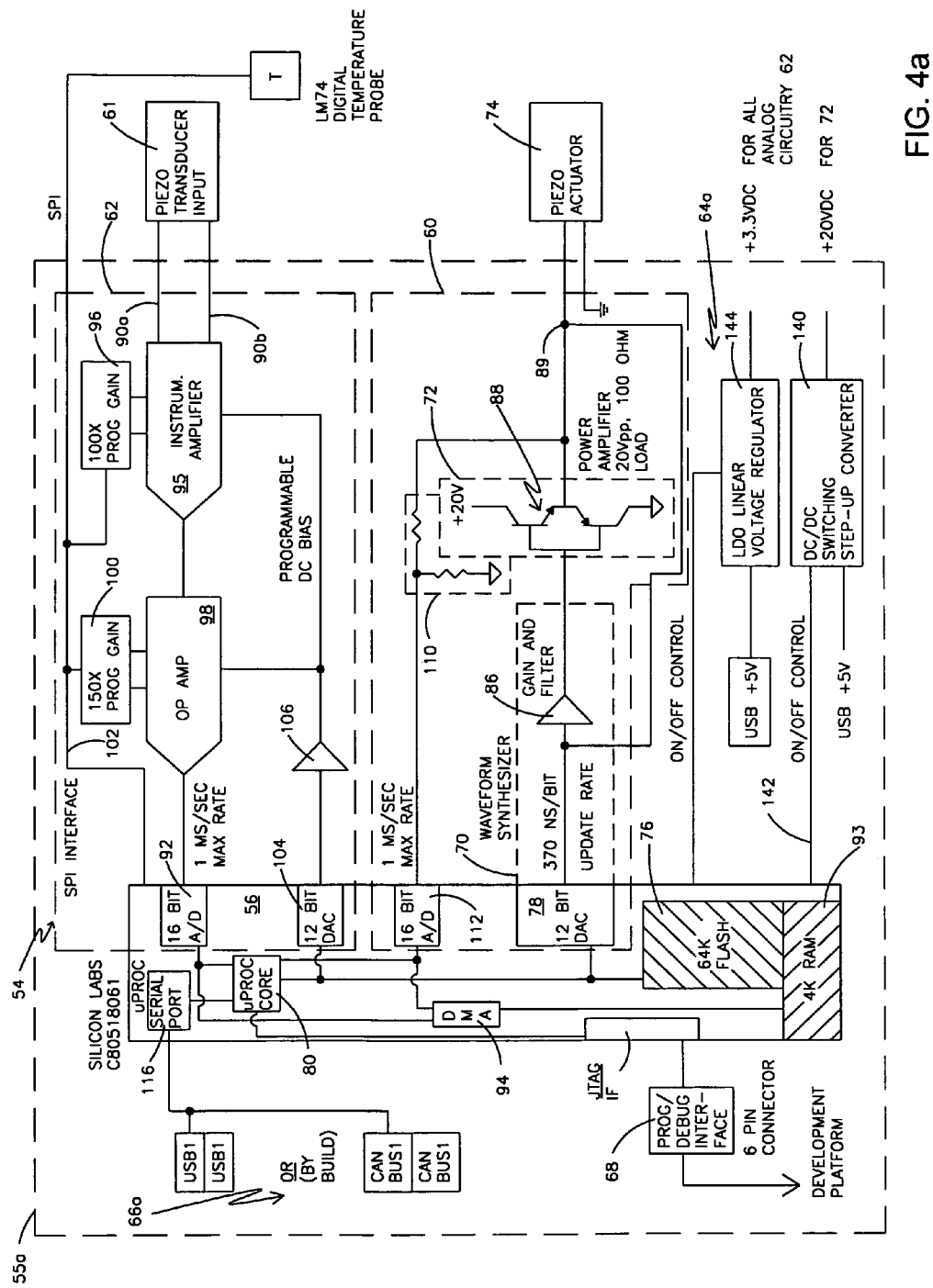
FIG. 4a is a block diagram of one embodiment of the miniaturized electronics for providing a desired signal to a piezoelectric actuator and for receiving a response with a piezoelectric sensor, in which a wired connector, such as a USB port or CAN BUS is used for providing communications and power.

Communications link 66a, 66b can be used for such things as transmitting data collected by sensor 61, for transmitting loaded waveforms obtained through A/D converter 112, for transmitting results of analysis as calculated by microprocessor core 80, for receiving commands from a base station, and for uploading additional waveforms to flash memory 76. The communications can be by way of a wire, such as a USB, RS232, RS485, or CAN BUS, as shown in FIG. 4a, any of which can be connected to serial port output 116 of microcontroller 56. Communications can also be wirelessly through a transmitter and receiver or through transceiver 120 provided with miniaturized electronics 54 as shown in FIGS. 4b-4d.

Figure 4B:
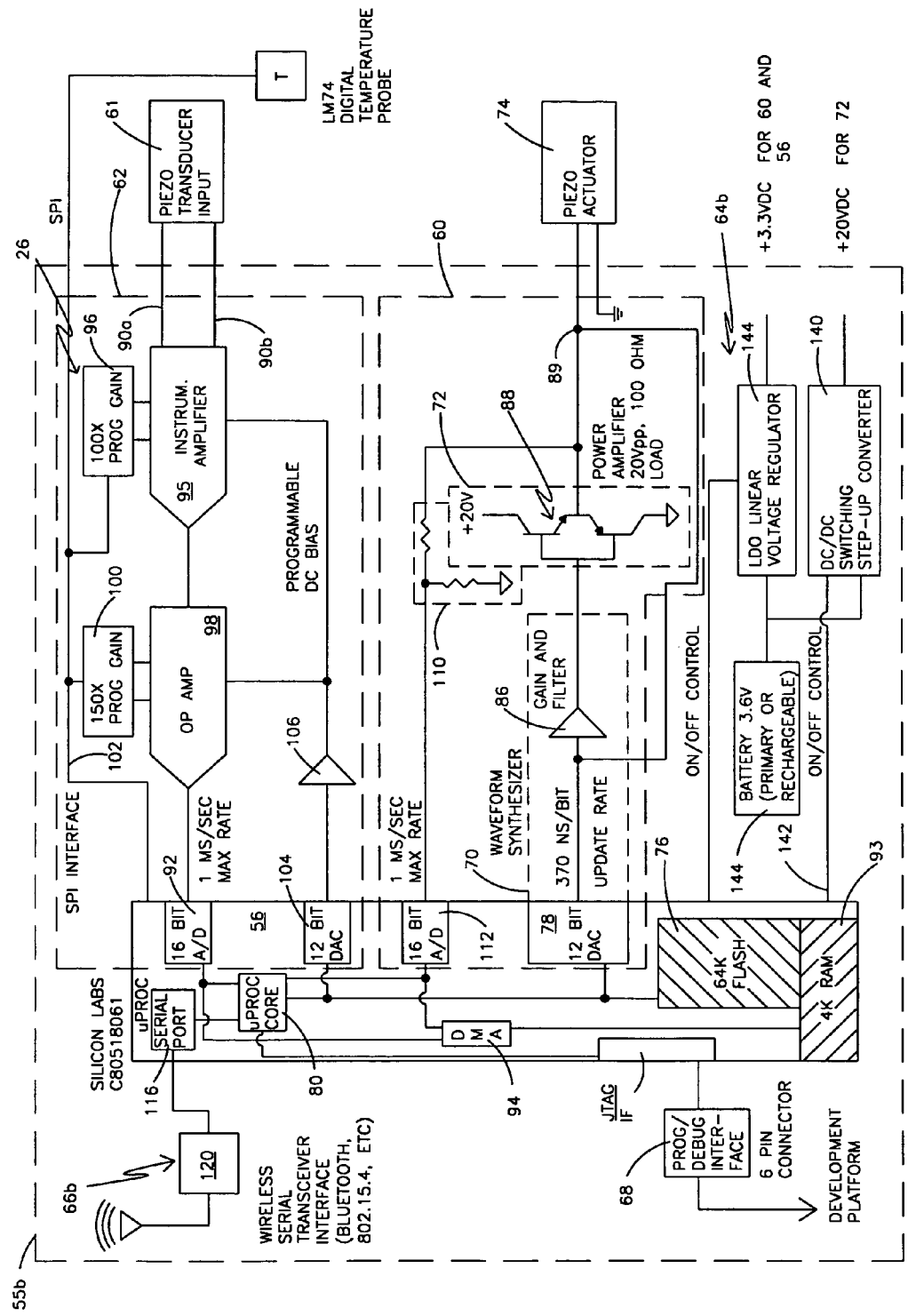
FIG. 4b is a block diagram of one embodiment of the miniaturized electronics for providing a desired signal to a piezoelectric actuator and for receiving a response with a piezoelectric sensor, in which a wireless serial transceiver is used with a battery power supply.
Figure 4C:
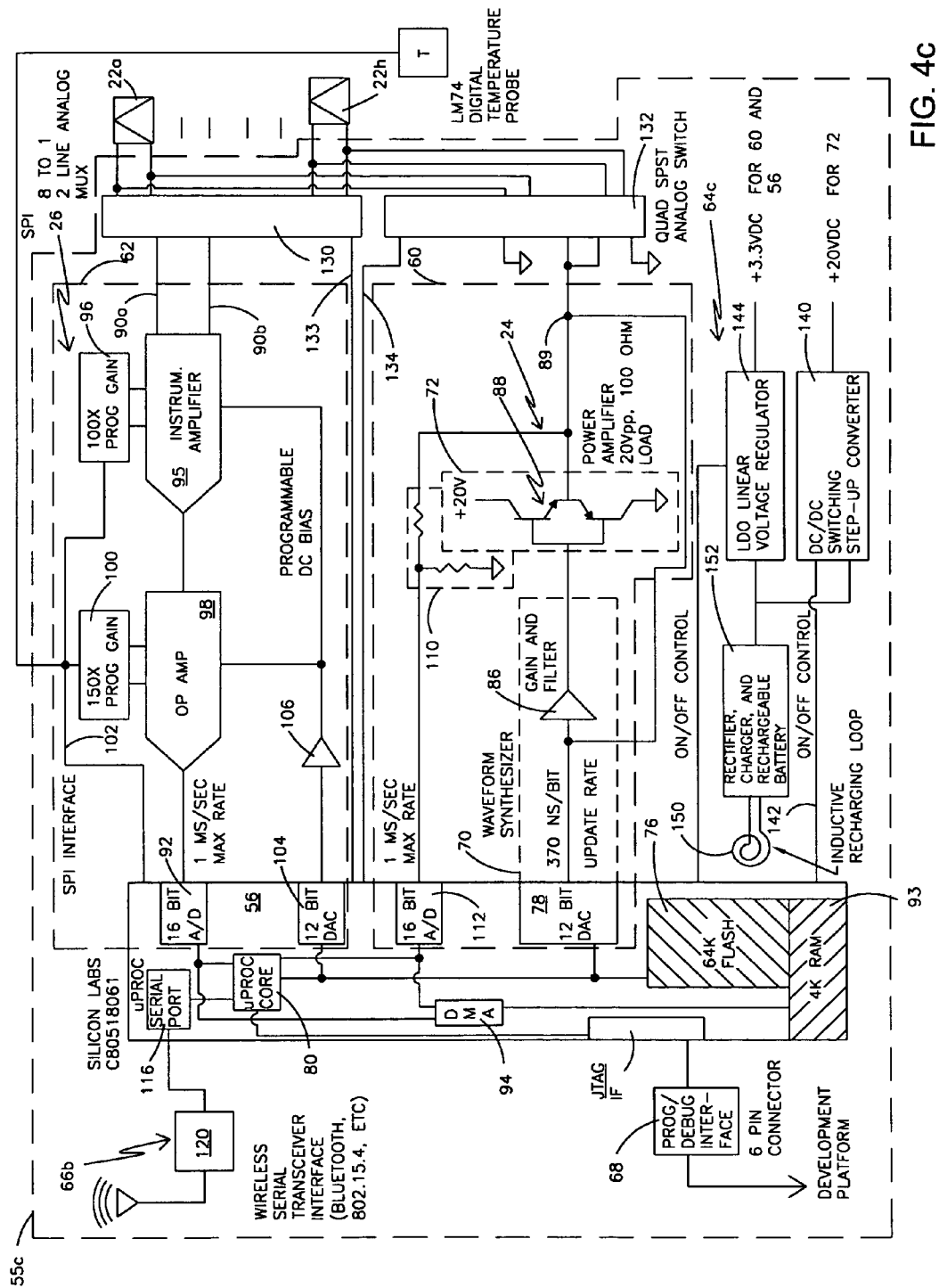
FIG. 4c is a block diagram of one embodiment of the miniaturized electronics for providing a desired signal to one of an array of piezoelectric actuator/sensors and for receiving a response with another of the piezoelectric actuator/sensors, in which a wireless serial transceiver is used with an inductive recharging loop for charging a rechargeable battery.
Figure 4D:
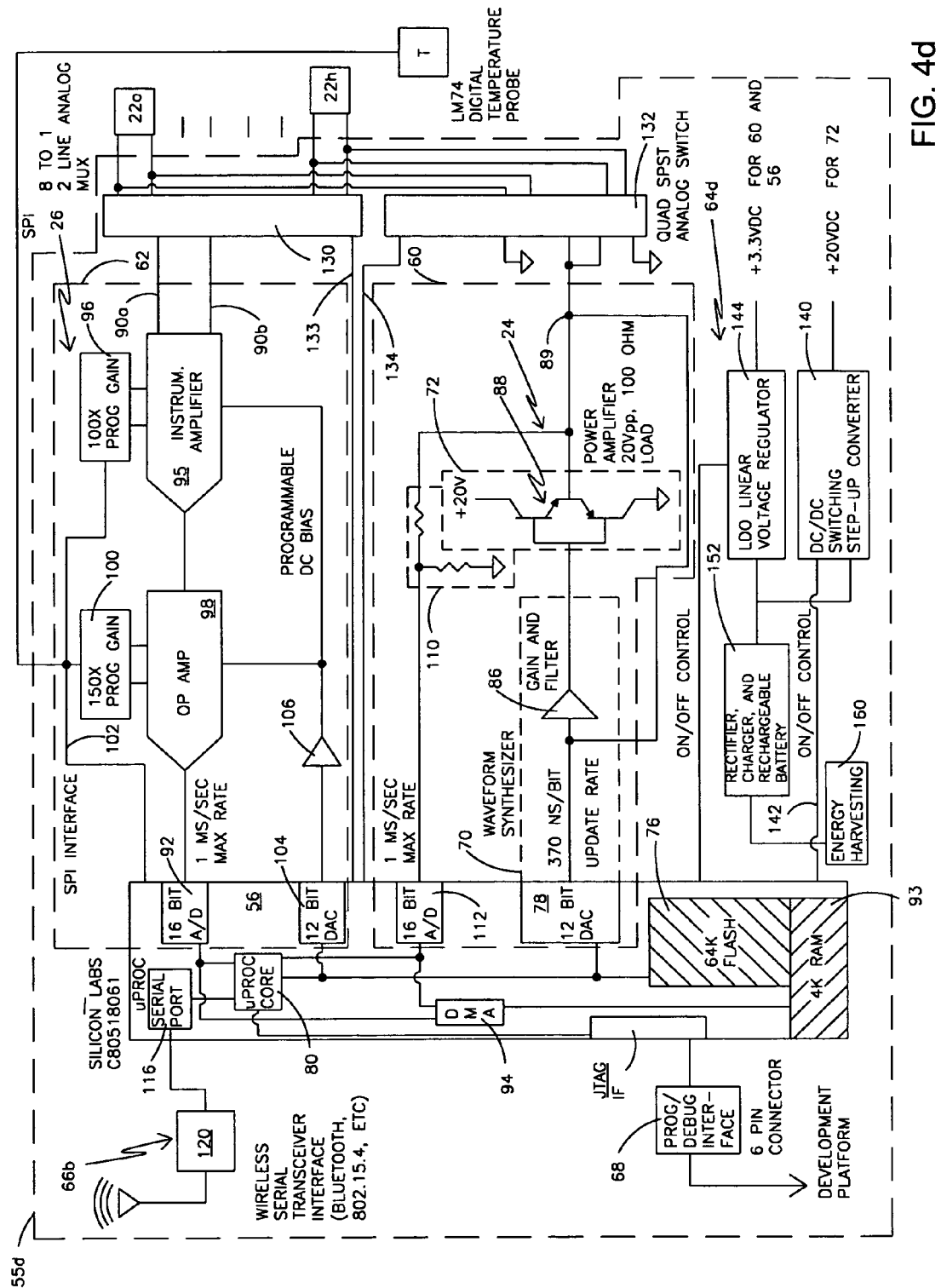
FIG. 4d is a block diagram of one embodiment of the miniaturized electronics for providing a desired signal to one of an array of piezoelectric actuator/sensors and for receiving a response with another of the piezoelectric actuator/sensors, in which a wireless serial transceiver is used with an energy harvesting device for charging a rechargeable battery.

A single sensor 61 may be connected to each circuit board 55a, 55b with miniaturized electronics 54 to collect sensor data and provide it to digital recording device RAM 93 or flash memory 76, as shown in FIGS. 4a, 4b. Alternatively, several actuator/sensors 22a, . . . 22h can be used to provide stimulation to substrate 32, as shown in FIGS. 4c, 4d and to receive data. Eight-to-one two-line analog multiplexer 130 and quad single pole single throw (SPST) analog switch 132 can be provided, as shown in FIGS. 4c, 4d, so that several actuator/sensor 22a . . . 22h can be operated together as actuators 27 or as sensors 29. Actuation is provided when switch 132 is positioned to allow a pulse from pulse power amplifier 72 to pass through switch 132 to particular sensor/actuator 22n. One or more of the actuator/sensors 22m other than sensor/actuator 22n is then sampled to record the signal received from substrate 32 derived from the actuation pulse provided by sensor/actuator 22n. That data is recorded as described herein above. Sensing with one of the actuator/sensors 22m can be simultaneous with actuation. Different sensors 22m can be switched in sequentially using multiplexer 130. Alternatively, an actuation signal from actuator 22n can be provided repeatedly one for each sensor 22m.

Only one pair of lines on the right of MUX 130 is connected to the pair of lines on the left of MUX 130. The pair of lines that are so connected is determined by control signals on digital I/O control lines 133 from digital I/O pins on microcontroller 56 under control of a program running on microprocessor core 80. Similarly, electronic switch 132 has digital I/O control lines 134 connected to digital I/O pins on microcontroller 56. Control lines 133 and 134 determine, for example, the position of switch 132, which sensor/actuator 22n is being stimulated to be an actuator and which sensor/actuator 22m is providing received data through multiplexer 130. Multiplexer 130 can be a MAX397 and electronic switch 132 can be a MAX4622, available from Maxim Integrated Products, Sunnyvale, Calif.

In one embodiment data from several of the sensors is recorded, and MUX 130 sequentially connects the different actuator/sensors 22m to provide that data for recording. In another embodiment, sensor/actuator 22a may be actuated and sensor/actuator 22h receives data. Then sensor/actuator 22h may be actuated and sensor/actuator 22a receives data.

In one embodiment receipt of data by sensor/actuator 22m is simultaneous with actuation by sensor/actuator 22n. If there is significant spatial separation between the two actuator/sensors 22n, 22m however, the time to begin recording received data in sensor/actuator 22m may be delayed to account for the time of flight for the signal. If several actuator/sensor are at different distances, data may be received and recorded from each sequentially as determined under program control and the delay for each may be different. One actuation signal can be provided and data from that signal recorded from one or more of the actuator/sensor 22m. Alternatively, a separate actuation signal can be provided for each measurement by the other actuator/sensor 22m.

These received data from the several sensor/actuators 22a . . . 22h acting as sensors is amplified and conditioned by programmable amplifiers 95 and 98 before being converted by A/D converter 92 to a digital signal for storing in RAM 93 or flash 76 as described herein above for a single sensor 61.

Quad SPST switch 132 has two pairs of lines on each side. Its switches are set under microprocessor program control so one pair of switches is open and one pair of switches is closed, thus selecting one pair of wires on its right side providing signal from power amplifier 72 to a single sensor/actuator 22n at a time. Additional quad SPST switches 132 can be provided so that any of the eight actuator/sensors 22n can be driven by the actuating signal from power amplifier 72.

Voltage conversion electronics can be connected to provide the voltage required by SSDD 74, 22n. For example a PZT actuator may require 20 volts, and voltage conversion electronics 140, such as the DC/DC switching step-up converter, can be used, as shown in FIG. 4a. Other actuators may require as much as 100 volts. Voltage conversion electronics 140 may be provided between microprocessor 56 and actuator 74, 22n. Microcontroller 56 can turn off actuator 74, 22n by providing a control signal to high voltage conversion electronics 140 along line 142, thus turning off signal generator circuit 60 to save power. Similarly, microcontroller 56 can turn off regulator 144 that regulates power derived from USB or CAN BUS connector 66a and that is used for operating analog circuitry in sensor input circuit 62, thus turning off sensor input circuit 62 to save power.

Energy for operation of electronics on board 55a can be provided through wired connector 66a, such as the USB port, as shown in FIG. 4a. For wireless devices energy can be provided using energy storage device 144, such as a battery, as shown in FIGS. 4b-4d. The battery can be a primary battery, or a rechargeable battery, such as a thin film battery. A capacitor can also be used. Energy storage device 144 may be connected to provide power to run programmable signal generator 60, a digital recording device, such as RAM 93 and flash memory 76, and communications link 66b. A second energy storage device can be provided which is connected to provide a high current pulse when needed, as described in U.S. patent application Ser. No. 10/379,223, and in U.S. patent application Ser. No. 10/769,642, both incorporated herein by reference.

Inductive loop 150, connected to a rectifier and charger, is used to recharge rechargeable energy storage device 152, as further described in commonly assigned patent application number US 2004/0113790 to Hamel et al., "Remotely Powered and Remotely Interrogated Wireless Digital Sensor Telemetry System," incorporated herein by reference. The patent application describes remotely providing an electromagnetic field that can be used to power the electronics in an embedded device and to read data collected. Rechargeable energy storage device 152 includes a rectifier and charger as well as a rechargeable battery or capacitor, as shown in FIG. 4c. A source of magnetic field (not shown) is brought near inductive recharging loop 150 to provide the power.

The battery charger can be coupled to receive power with energy harvesting apparatus 160 for harvesting ambient energy in its environment, as shown in FIG. 4d. The energy harvesting apparatus 160 can be of a type to convert light, vibration, or mechanical movement into electricity for charging rechargeable storage device 152 and operating electronics on board 55d. A paper, "Power Management for Energy Harvesting Wireless Sensors," by Steven Arms, Christopher Townsend, David Churchill, and Jake Galbreath, incorporate herein by reference, submitted to SPIE's Symposium on Smart Structures & Materials, San Diego, Calif., March 2005, also describes power management techniques to get batteries to last a long time. US Patent application number US 2004/0078662 to Hamel et al., "Energy Harvesting for Wireless Sensor Operation and Data Transmission," incorporate herein by reference, describes a scheme to provide energy using energy harvesting.

In one embodiment microprocessor core 80 can run a program to direct switch 132 to provide actuator/sensor 22 to perform as actuators 27 to direct stimulation into substrate 32 first and then to activate switch 132 in time to provide actuator/sensor 22 to perform as sensors 29 to detect signal in substrate 32.

In another embodiment, microprocessor core 80 can run a program directing one of the actuator/sensor 22 to perform as actuator 27 sending out a stimulation signal to substrate 32 while the other actuator/sensors 22 act as sensors 29 to sense the signal traveling in substrate 32.

Figure 4E:
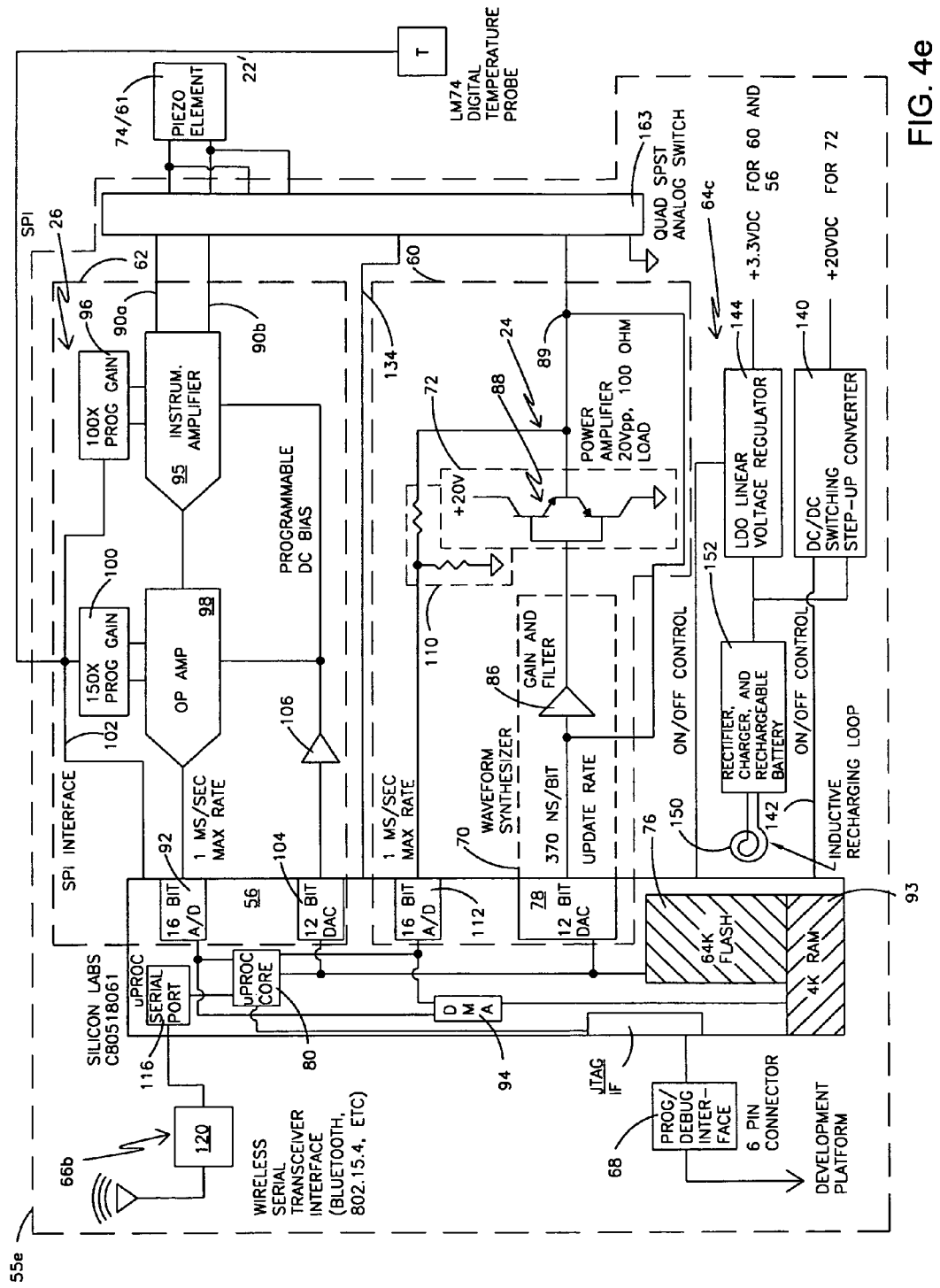
FIG. 4e is a block diagram of one embodiment of the miniaturized electronics for providing a desired signal to a piezoelectric actuator/sensor and for receiving a response with that same piezoelectric actuator/sensor, in which a wireless serial transceiver is used with an energy harvesting device for charging a rechargeable battery and a single piezo element is used to provide both actuation and sensing functions.
Figure 5B:
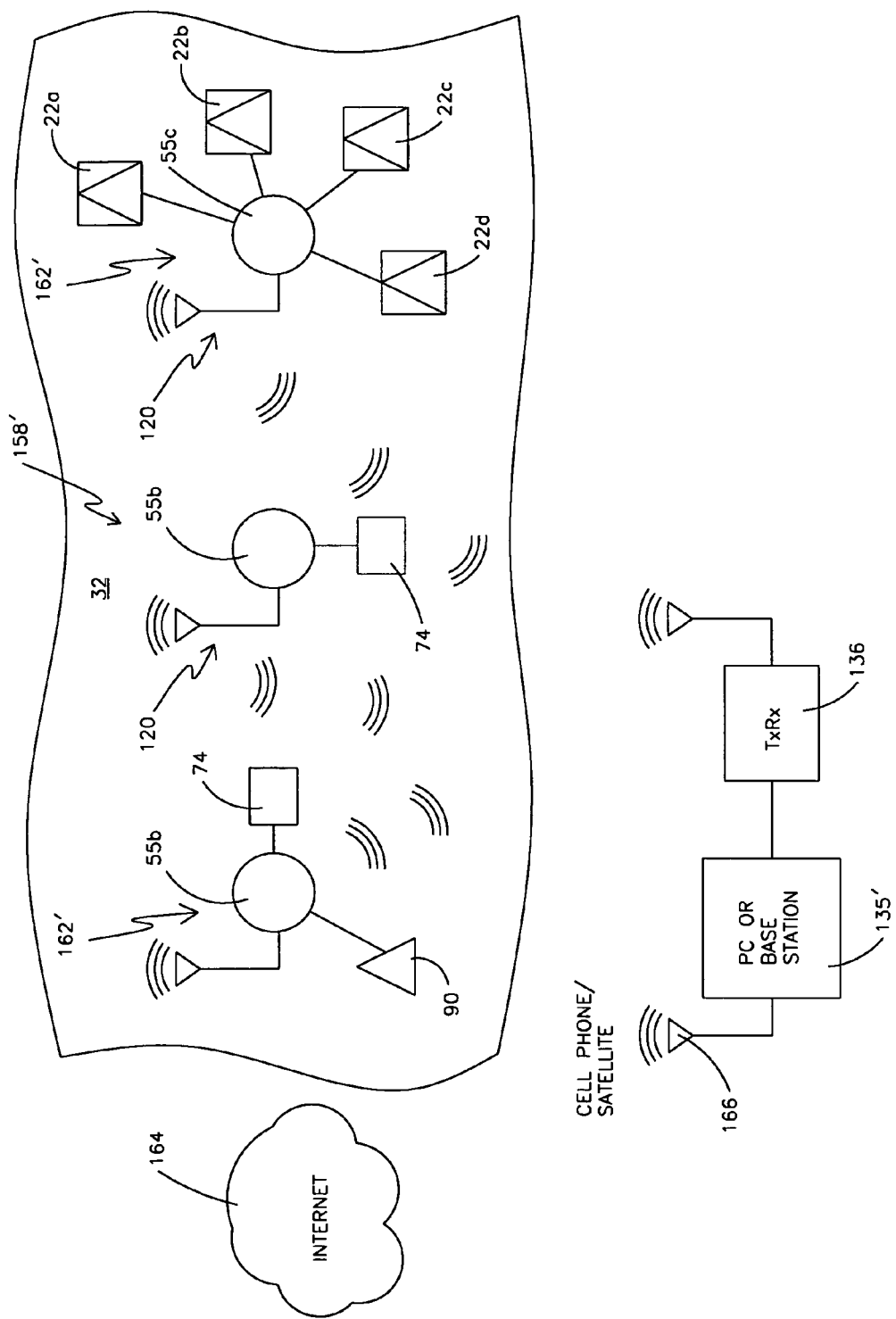
FIG. 5b is a schematic diagram showing an array of smart actuator/sensors linked together with a wireless interface.

In another embodiment array 158, 158' of modules 162, 162' is mounted on substrate 32 as shown in FIGS. 5a, 5b. Each module 162, 162' of array 158, 158' includes board 55a, 55b, 55c, 55d, 55e (FIGS. 4a-4e) including microcontroller 56. Each module 162, 162' includes at least one sensor/actuator 22, 22a . . . 22d or individual actuator 74 and individual sensor 61. Each module 162, 162' in array 158, 158' can include an address that base station 135, 135' can use for identifying each module 162, 162' in the wired or wireless array 158, 158'.

Each module 162, 162' of array 158, 158' can also have its own communications link 66a, 66b. Since they are addressable, several modules 162, 162' can also be wired to the same communications link, such as network wire 163.

Software running on microprocessor cores 80 within each microcontroller 56 can program each sensor/actuator 22, 22a . . . 22d to perform as either actuator 27 or as sensor 29 using address specific commands, and the role each performs can change with time.

Multiple stimulation signals may be sent out by sensor/actuator 22, 22a . . . 22h performing as actuator 27 of module 162. Multiplexer 130 and switch 132 are used to provide the actuation pulses to actuator 27n and to acquire data for recording from each sensor 29 of actuator/sensors 22, 22a . . . 22h. The data from all sensors 29 of array 158 of actuator/sensors 22a . . . 22h is sequentially recorded in RAM 93 of microcontroller 56 and can later be analyzed by software running on microprocessor core 80 to determine properties of substrate 32, such as curing, dielectric constant, and presence and location of defects, such as cracks and corrosion. Alternatively, the stored data can be transmitted to base station 135, 135' for analysis there, as shown in FIGS. 5a, 5b.

Once substrate 32 has been stimulated and sensor data has been recorded, a program running on microprocessor core 80 can then direct that a different one of actuator/sensor 22, 22a . . . 22h perform as actuator 27 to send out a stimulation in substrate 32 while sequentially switching others of actuator/sensors 22, 22a . . . 22h act as sensors 29 to sense the signals arising in substrate 32 from that stimulation. Microprocessor core 80 can cause this to change to happen by controlling MUX 130 and switch 132, as shown in FIGS. 4c, 4d. The data recorded based on the signal from this different actuator can be used to provide further information about substrate 32.

Alternatively, a program running on microprocessor core 80 can direct that one of actuator/sensors 22, 22a . . . 22h perform as actuator 27 to send out repeated stimulations in substrate 32 while sequentially switching others of actuator/sensor 22, 22a . . . 22h to act as sensors 29 to sense the signals arising in substrate 32 from those repeated stimulations.

Single piezo element 22' can be used to provide both actuation and sensing functions, as shown in FIG. 4e. Actuation is provided through quad single pole single throw analog switch 163 followed by sensing through that same switch 163. Delay in providing this switching function is on the order of about 200 nS so this single piezo element 22' embodiment can be used for applications in which such delay between actuation and sensing is acceptable. For reflection measurements, for example, a single piezo element can be used if the distance of an anticipated reflection is great enough that time for the reflected wave to return is greater than 200 ns.

A single piezo element can provide material properties from such parameters as damping time of the piezo element and from the initial amplitude of the piezo element. One can measure one or both of these parameters at several frequencies or scan over frequencies to obtain spectral characteristics of these parameters that can give particularly important information about mechanical properties of the material. A temperature sensor, such as a thermocouple, thermister, or digital temperature probe can be used in conjunction with such measurements. Digital temperature probe T, such as LM74 from National Semiconductor, Santa Clara, Calif., can be monitored over SPI 102, as shown in FIGS. 4a-4e and FIGS. 8a-8c. A heater (not shown) can be provided to ensure that measurements taken at different times are taken at the same temperature or to provide mechanical and electrical property measurements over a range of temperatures, similar to the heater used for measurements in tissues, as described in U.S. Pat. Nos. 6,832,111 ("the '111 patent"), and 6,807,444 ("the '444 patent"), incorporated herein by reference and further described herein below.

The circuits of the present apparatus can be used to measure parameters of oil flowing in a pipeline. They can also be used to measure parameters of oil lubricating an internal combustion engine, as described in U.S. Pat. Nos. 6,853,203, 6,854,325, 6,845,660, and US patent application 2003/0222656, all of which are incorporated herein by reference. It can also used to indicate that oil within a vacuum pump needs to be replaced. It can similarly be used to measure impurities in water or another fluid, measuring particulates or contaminants in air, measuring parameters of blood, such as viruses. It can also be used to measure corrosion, as described in U.S. Pat. Nos. 5,260,666, 5,338,432, 5,445,178, 5,479,104, and 5,859,537, all of which are incorporated herein by reference. Also to measure parameters of soil, as described in U.S. Pat. Nos. 4,288,742 and 6,477,907, both incorporated herein by reference, and to measure curing of a material, such as concrete, as described in U.S. Pat. No. 6,819,121, incorporated herein by reference.

In yet another embodiment a network of modules 162, 162' can be used to provide simultaneous sensing and storage of data, as shown in FIGS. 5a, 5b. Transmission can be wired, for example along a USB connector as shown in FIG. 5a or it can be wireless as shown in FIG. 5b. Module 162, 162' can receive commands from base station 135, 135' through its wired communications port 66a or its wireless communications port 66b. Module 162, 162' can also receive commands through another module 162, including from a higher level module in a hierarchical arrangement. A user program in flash memory 76 of microcontroller 56 interprets these commands and directs operation of on board electronic hardware. Base station 135, 135' can broadcast commands to all modules 162, 162' of array 158, 158' at once or addressed to individual modules 162, 162' using that module's address. Modules 162, 162' can also communicate their data or results to base station 135, 135'.

Base station 135, 135' can be located on substrate 32 or it can be separate from substrate 32, as shown in FIGS. 5a, 5b Base station 135, 135' can include a personal computer. Base station 135' can have its own transceiver 136 for wireless communication with modules 162', as shown in FIG. 5b. Base station 135' can also have a wired or wireless communications link with a host computer, for example, through the internet 164. The communications link can be via cell phone or satellite phone 166.

If a command to begin actuation and collecting data is broadcast by base station 135, 135', actuators 74 or actuator/sensors 22a . . . 22h excite their piezo elements. Excitation can be set to occur immediately or after a pre-programmed time period. Actuator/sensors 22a . . . 22h configured as sensors 29 then begin to receive data, and they may begin receiving immediately or after a pre-programmed time period for recording in RAM 93. Data from all sensors 61, 22a . . . 22h linked to microprocessor core 80 and memory device 93 in that module 162, 162' may then be transferred to another memory device, such as non-volatile memory. These data include time, voltages as well as test ID, date, and other testing parameters. Various schemes for providing the calendar date can be provided, including using the crystal oscillator and periodically communicating the date over communications link 66a, 66b. Data stored in RAM 93 of microcontroller 56 can include received sensor data and timing information so the time the actuator was actuated and the time the sensors received the signals are both recorded.

The recorded data can be locally analyzed in microprocessor core 80. Alternatively the data can be downloaded to base station 135, 135'. Thus, nearly simultaneous data collection from multiple points on the substrate can be achieved. Data can be autonomously relayed through internet 1164 to an internet based server by base station 135, 135'. A PC based program running on this server can perform further analysis from data received by base station 135, 135' or data relayed to the internet based server.

Figure 6:
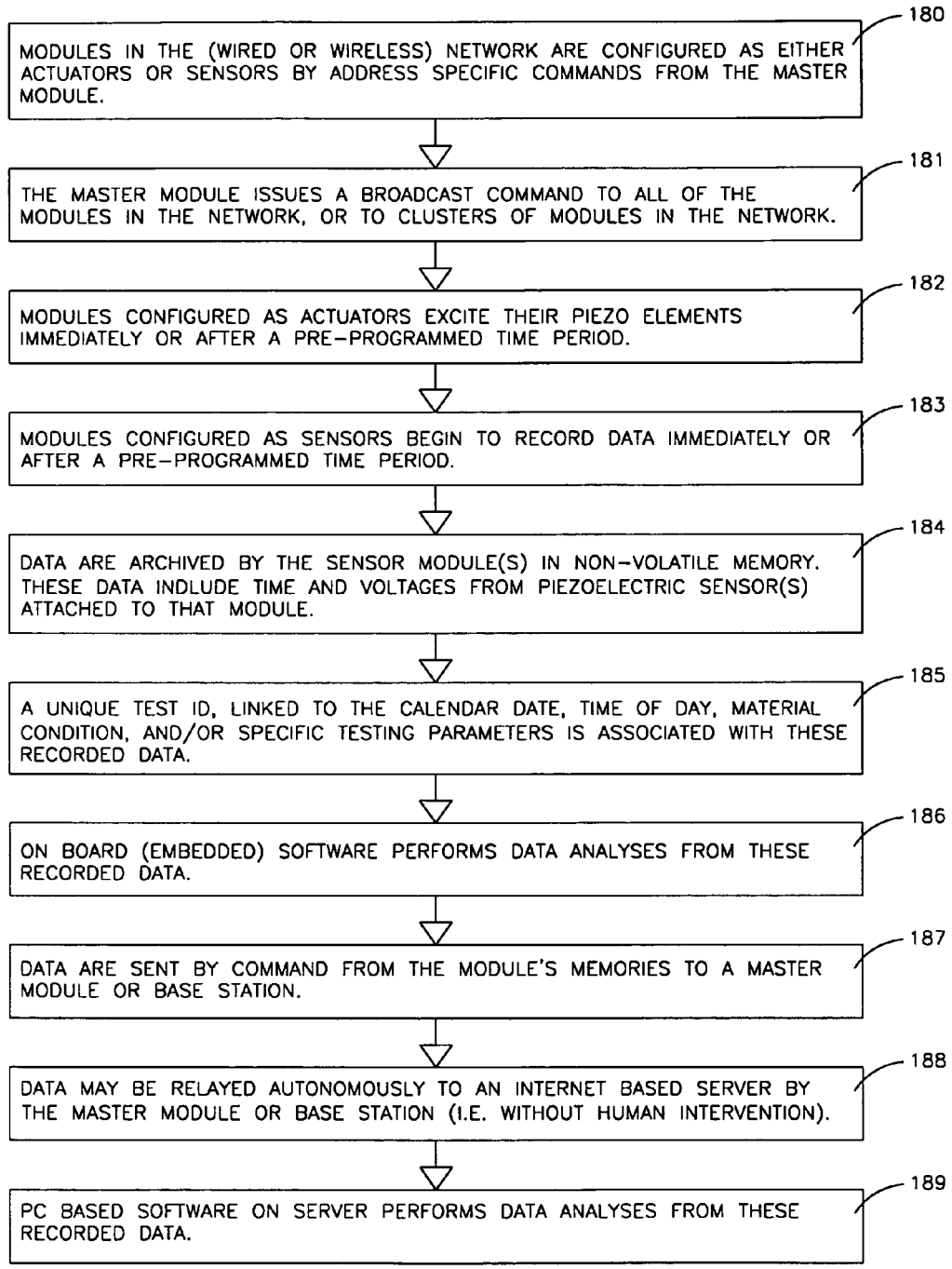
FIG. 6 is a flow chart of a methodology of the present application for actuator/sensor data acquisition.

In one embodiment base station 135, 135' sends commands wirelessly or along network wire 163 to address specific ones of modules 162, 162' that are members of array 158, 158' and configures one or more of these modules to perform as actuator modules 27 and configures one or more others of these modules 162, 162' to perform as sensor modules 29, as shown in box 180 of the flow chart in FIG. 6. Thus, actuator signals may be provided by one or more actuator/sensors 22a . . . 22h acting as actuator modules 27 of array 158, 158' while other actuator/sensors 22a . . . 22h act as sensors 29 and sense the signals coming from the substrate, while module electronics records, analyzes, and/or transmits the data, as further described herein below.

Next, base station 135, 135' issues a broadcast command to all modules 162, 162' in array 158, 158', including those configured as actuator module 27 and those configured as sensor module 29, as shown in box 181. The broadcast command may also be issued to a subset of modules 162, 162' in array 158, 158'.

The broadcast command initiates a program to run on microprocessor core 80 in actuator modules 27 to excite their piezo elements immediately or after a pre-programmed time period, as shown in box 182. Actuator modules 27 may record the actuation signal and the time stamp of that signal. That data is later transmitted to base station 135, 135' and used in the analysis along with the time stamped sensor data.

A program running on microprocessor core 80 in sensor modules 29 provides that data from sensors 61 is recorded in RAM 93, as shown in box 183. Data may be recorded beginning immediately or after a pre-programmed time period. Parameters of the program, such as setting a delay time period before beginning recording, may be determined by commands from base station, 135,135', and these commands may be stored in flash memory 76 in sensor modules 29, as further described herein below.

Data may be archived by the sensor modules 29 in non-volatile flash memory 76, as shown in box 184. The data may include the time data was received and the voltage level obtained from piezoelectric sensor 61 connected to that sensor module 29. The data is thus stored locally within module 162, 162' until called for by base station 135, 135'. The stored data can include the time the data was recorded, allowing associating data from several sensors in base station 135, 135'.

In addition, a unique test ID is recorded associated with the recorded sensor data, as shown in box 185. The test ID may be associated with a setup including calendar date, a time of day, and/or specific testing parameters, such as temperature, wave form used for stimulation, drive voltage, and the material under test. In addition, actual measurements of actuator drive signal and sensor data can be recorded by modules acting as actuators 27 and modules acting as sensors 29 respectively.

Software embedded in flash memory 76 may be run on microprocessor core 80 to analyze the data recorded in RAM 93 or archived in flash memory 76, as shown in box 186.

Data may then be sent to a master module or to base station 135, 135' as provided in the program running on microprocessor core 80, as shown in box 187. Transmission my be controlled by the master module or base station 135, 135' so that a particular actuator/sensor 22m acting as a sensor module 29 transmits data upon receipt of its unique address from base station 135, 135'.

Data may also be relayed to internet based server 81 by the master module or base station 135, 135', as shown in box 188 for display on a web site. The data can thus be archived on a computer server.

PC based software running on internet based server 81 can perform data analyses on data recorded by server 81, as shown in box 189, and this analysis can be performed under program control, autonomously, and without human intervention.

A flow chart for two separate programs stored in flash memory 76 for running on microprocessor core 80 is provided in FIGS. 7a-7d for single module 162, 162' with single actuator 74 and single sensor 61. Generally the flowchart also applies to a several sensor/actuator set up.

Alternative approaches to handling data are also possible. For example, data can be immediately transferred to base station 135, 135' or internet server 81 during acquisition. In this embodiment no data analysis would be performed in module 162, 162'.

Software to direct internal electronic hardware functions of module 162, 162' is described in FIGS. 7a-7d. While the "bootloader" is the program that is first encountered at power up, or at "start," its only function is to control operation while the second program, called "the main program loop," is being updated or replaced. Under ordinary use when modules are in use to provide stimulation and receive sensor data, the bootloader program passes control to the main program loop and the bootloader program is not used. The program commands pass right through and none of the bootloader program is used. Under extraordinary circumstances, such as when flags are set in the main program loop under external electronic command, the bootloader program is selected, and control is given over to it for the purpose of replacing the main program loop program. The bootloader program thus allows the array commanding it to replace the "the main program loop" with an updated or changed version. This update function is accomplished by reading the new main program loop byte by byte from the microcontroller serial port and writing it to the prescribed location in the microcontroller's flash memory. After the updated program is stored in memory, program control is returned to the new main program loop.

Figure 7A:
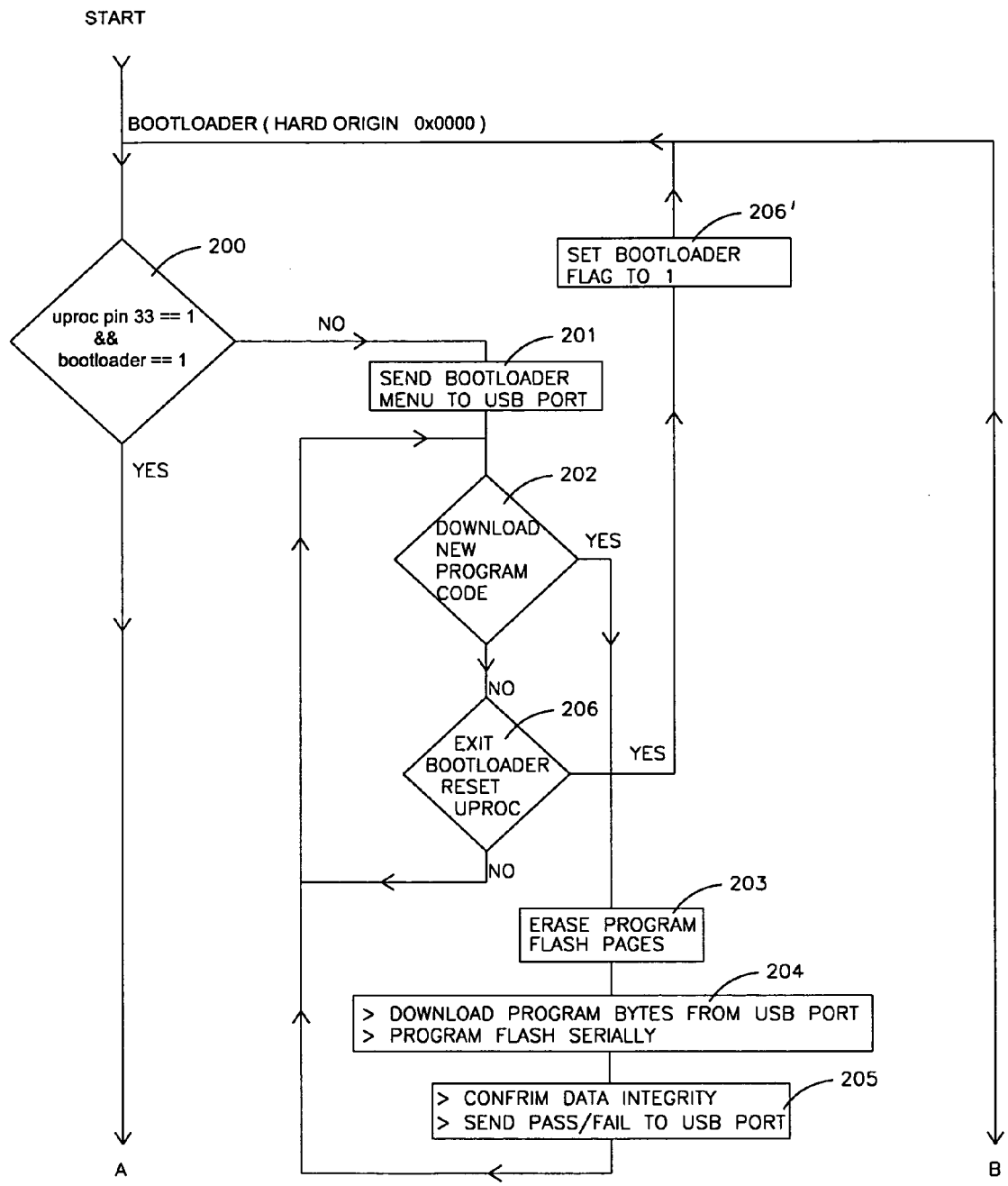
FIGS. 7a-7d is a flow chart showing software running on the microprocessor of FIGS. 4a-4e for a module including an actuator/sensor
Figure 7B:
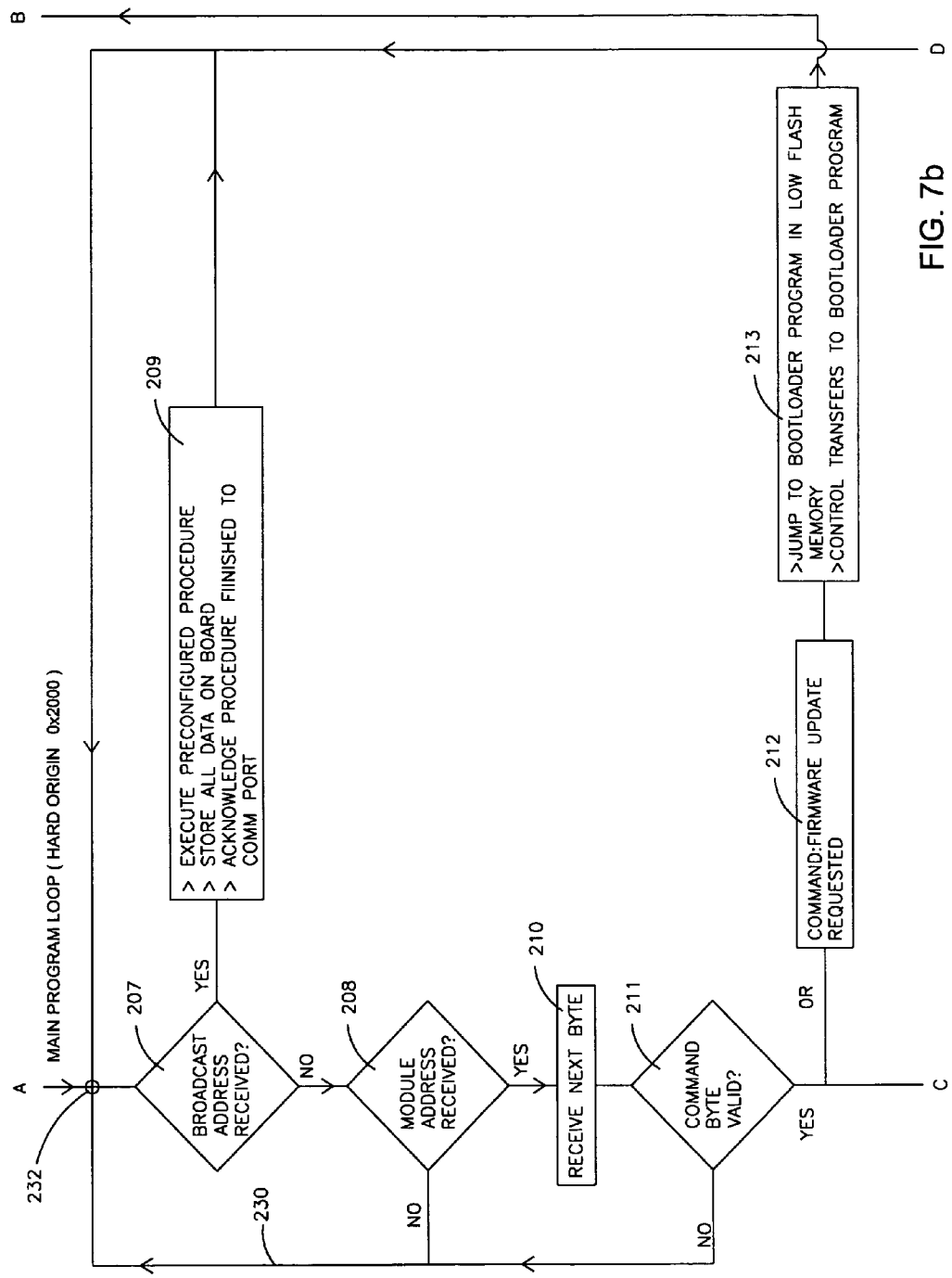

Two flags may be set in the main program loop and are interrogated in the bootloader program, as shown in decision box 200 of FIG. 7a. One is a physical pin on the processor that can be controlled externally to force the bootloader program to run so that an operator can replace the main program loop. The other is a flag that can be set in the main program loop. If both flags are set to 1, which is the ordinary state, the bootloader is not used. The processor exits the bootloader program along line A and goes to the main program loop, as shown in FIG. 7b.

If either the bootloader flag is set to zero or if the external physical pin is set to 0, for example, if the operator sets the external pin to 0 at power up when the microprocessor resets, the bootloader sends a menu through its communication port, such as a USB or wireless device, offering choices to the operator, as shown in box 201. The menu may include choices, such as replace the main program loop or exit the bootloader program. Based on the response of the operator to those choices, the bootloader program decides whether to download the new program code, as shown in box 202. If yes then the part of flash memory 76 that contains the main program loop is erased, as shown in box 203. Next the new program is downloaded using an appropriate communications protocol through the communications port. Each byte of the new main loop program is then stored into the memory locations, as shown in box 204.

In the next step, a check sum procedure or other checking method is used to test and compare the number with the number for the data transmitted by the master to confirm the integrity of the data stored in memory, as shown in step 205. The response will either be pass or fail. If the data passes then the bootloader resets the bootloader flag to 1. In either case this pass or failing response is sent back up to box 202 in which a menu is presented to the master along with the response about pass or fail. The master then chooses the appropriate menu item and decides whether to download new program code. If the answer to decision box 202 is no, then it further decides whether to exit the bootloader program, as shown in box 206. If the answer to decision box 206 is yes, the bootloader flag is set to 1, as shown in box 206', and the program proceeds to decision box 200. If the operator does not set the physical pin to 0 both flags will now be 1, and program control passes to the main program loop in FIG. 7b.

In normal operation the main program loop waits for and receives commands via serial port 116 of microcontroller 56. These commands direct the internal electronic hardware functions of module 162, 162'. The first bytes of a valid command sequence received at the serial port can be a generic address indicating that what follows is being "broadcast" to all modules 162, 162' from base station 135, 135 and is valid for all modules 162, 162' in array 158, 158' as shown in decision box 207. Alternatively, the first bytes of a valid command sequence received at the serial port can be the address of a particular module 162, 162', as shown in decision box 208.

If the first bytes are a broadcast address, each module 162, 162' executes a preconfigured procedure, stores data locally on board, and when the procedure is complete, acknowledges that the procedure is complete by sending a signal through its communications port 116, as shown in box 209. The module then awaits a further broadcast command or a command directed to its own node address, as shown by line D-F extending back to the beginning of the main program loop. If the first bytes are not a broadcast address the program then passes to box 208 to determine whether the bytes are those of its own address.

When a particular module 162, 162' receives its own valid address, as shown in box 208, it will then attempt to receive and interpret subsequent bytes received at its serial port as instructions and data from base station 135, 135, as shown in box 210. If so, it will determine whether the command byte is valid, as shown in decision box 211, in which the processor determines whether the command byte is the code of one of the valid commands.

If the command byte is valid the program executes that command. Such commands fall into three categories:

(1) instructions with data which will cause certain module parameters to set up;

(2) instructions and data which cause module 162, 162' to initiate actions, such as driving a piezo actuator with a pulse, digitizing piezo receiver data, recording sensor data, or sending recorded and stored sensor data to the internet; and (3) the instruction to execute a preconfigured set of category (1) and category (2) instructions in sequence without further interaction with base station 135, 135' until the preconfigured set of instructions is finished. For example, an instruction in category (3) allows base station 135, 135' to direct all modules 162, 162' on array 158, 158' to start a series of individual node tasks simultaneously, thus allowing data to be later collected and recorded from a large number of nodes with accurate time coherence.

Most of the specific commands described herein below have been implemented to run on miniaturized electronics on board 55a, 55b as shown in FIGS. 5a-5d. If the command byte is valid it may be one of the following nine commands, which is then executed. After execution of the command, module 162, 162' then awaits a further broadcast command or a command directed to its own node address, as shown by line D extending back to the beginning of the main program loop. The nine commands are:

"Firmware update requested" command, shown in box 212 directs the program to divert along line B to the bootloader program stored in flash memory, which as described herein above, controls the transfer of a new main program loop into flash memory, as described in box 213.

Figure 7C:
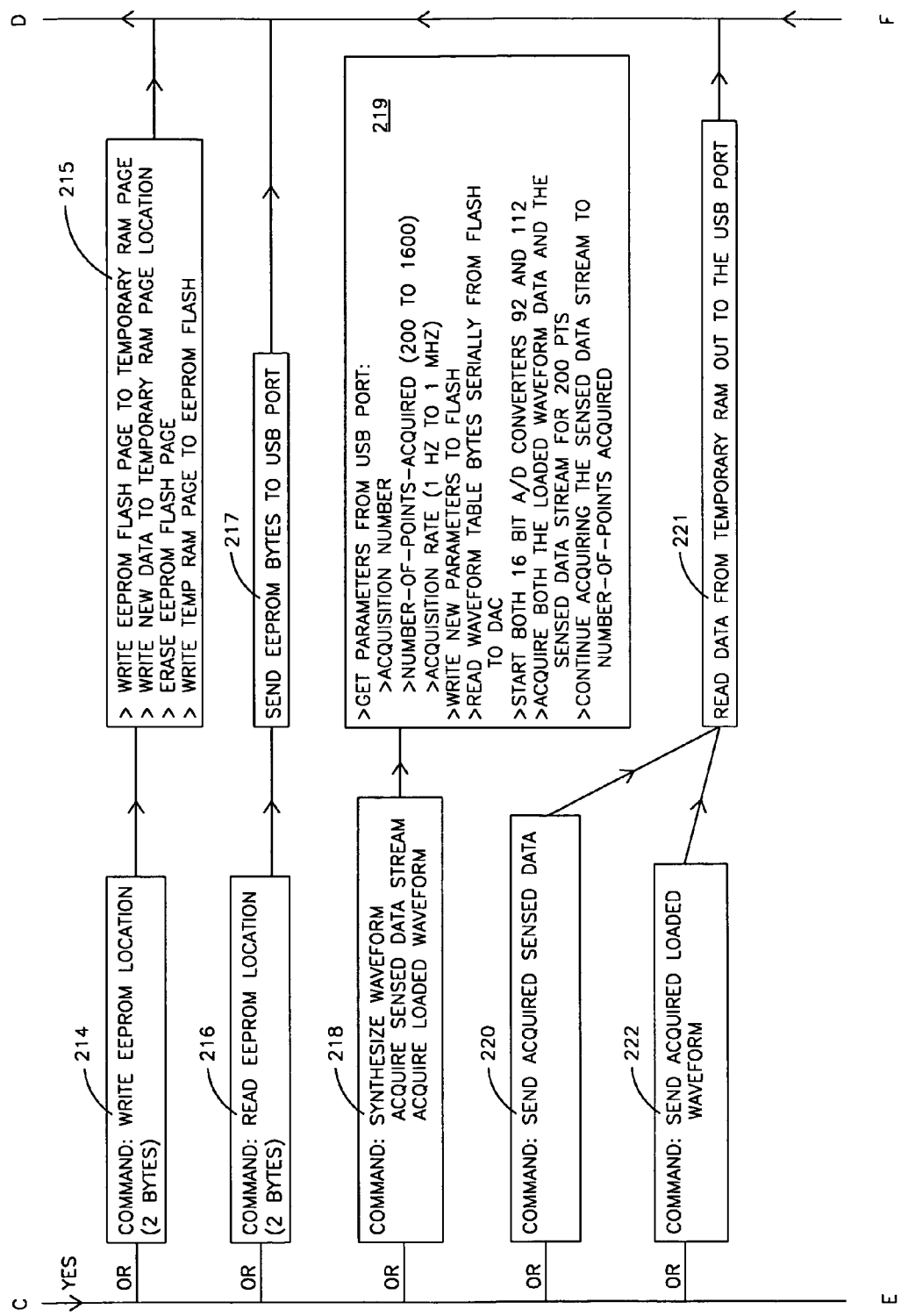

"Write eeprom location" command, shown in box 214 in FIG. 7c begins a sequence of steps for loading flash memory with information. The information may be data for parameters, such as gain, how many points of data are to be stored in memory during a run, and A/D converter rate. Following the bytes designating this command additional bytes follow with the data. The steps for executing this command include writing a flash memory page to temporary RAM storage, writing new data to a location on this page in temporary RAM storage, erasing this page in flash memory, and writing the temporary RAM page with its new data to flash memory, as shown in box 215.

"Read flash memory location" command, shown in box 216 begins a sequence of steps in which two bytes of data in flash memory 76 is read, directed to serial port 116, and transmitted to base station 135, 135.

"Synthesize wave form" command, shown in box 218 tells wave form synthesizer 70 which includes DAC 78 to provide a wave form based on data stored in memory 76. The command also starts 16 bit A/D converter 112 to look at the loaded wave form after amplification in pulse power amplifier 72 while it is driving piezo actuator 74, 22a . . . 22h, and store that loaded waveform in memory 93. The command also starts 16 bit A/D converter 92 to receive amplified data sensed by transducer 61, 22a . . . 22h, as also shown in box 218.

In operation the "synthesize wave form" command starts a series of steps. The first step includes obtaining data for parameters from base station 135, 135' through serial port 116, as shown in box 219. The parameters include an acquisition number or identification number for this particular run, the number of points of data to be acquired, which may be in the range from about 200 points to about 1600 points, and the data acquisition rate, which may be in the range from about 1 Hz to about 1 MHz. Next, these newly acquired parameters are written to flash memory 76. Waveform table bytes providing the waveform are then read from flash memory 76 to DAC 78, which provides the wave form to amplifiers 86 and 72, which drive actuator 74. Both 16 bit A/D converters 92 and 112 are started to acquire sensor data and loaded wave form data for the number of points of data to be acquired. After the wave form data has been outputted from wave form synthesizer 70 A/D converter 92 may continue acquiring data, for example, as there may be delay between stimulation and response.

"Send acquired sensor data out USB port" command, shown in box 220, is the command to read sensor data that was stored in temporary RAM 93 in the particular module 162, 162' to serial port 116 and from there using wired or wireless transmission to base station 135, 135', as shown in box 221.

"Send acquired loaded wave form data out USB port" command, shown in box 222 is the command to read loaded wave form data that was stored in temporary RAM 93 in the particular module 162, 162' to serial port 116 and from there using wired or wireless transmission to base station 135, 135', as also shown in box 221.

Figure 7D:
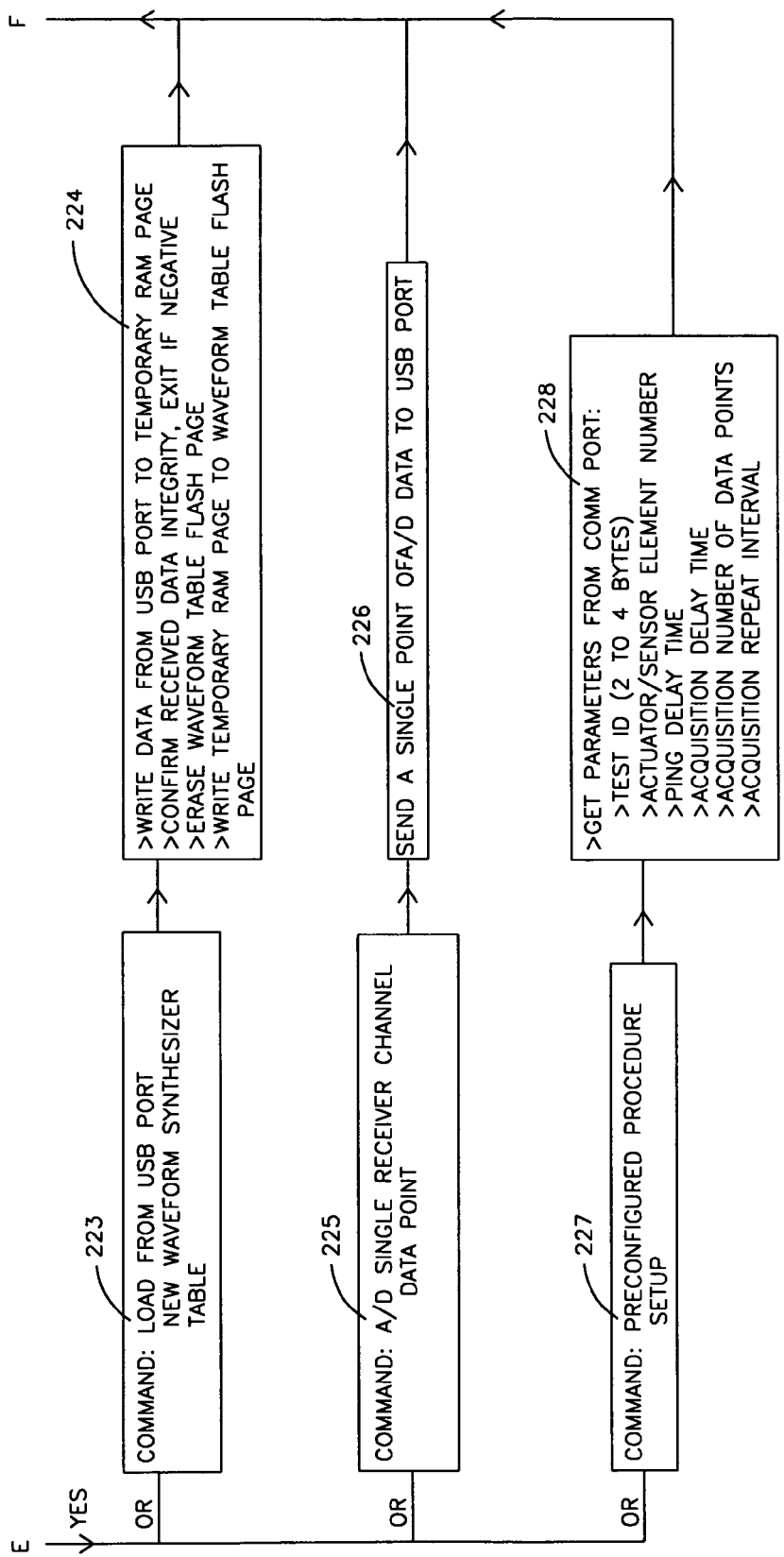

"Load from USB port new waveform synthesizer table" command, shown in box 223 in FIG. 7d begins a sequence of steps for loading flash memory with information to change the waveform being used to drive stimulation of actuator 74, 22a . . . 22h. Following the bytes designating this command additional bytes follow with the data for the new waveform table. The steps for executing this command include writing the new data as received at serial port 116 to a temporary RAM storage page, confirming the integrity of the received data, such as with a checksum, erasing the waveform table that was in flash memory, and writing the temporary RAM page with its new data to the waveform table in flash memory, as shown in box 224.

"Load single receiver channel data point" command, shown in box 225, begins a sequence of steps for using A/D converter 92 to convert 1 data point—2 bytes—and loading that single data point of received data from A/D converter 92 to serial port 116 for transfer to base station 135, 135', as shown in box 226.

"Preconfigured procedure setup" command, shown in box 227 is the command to read and load set up instructions and data into memory from base station 135, 135' so the module knows what to do when it receives a broadcast command from base station 135, 135'. Instructions and data to be obtained through serial port 116 during this command include a test ID number, such as a 2 to 4 byte number, an actuator/sensor module number, ping delay time, which is the time between wave forms sent to actuator 74, acquisition delay time, which is the delay time before a module acting as a sensor begins recording sensor data after the wave form has been sent out by DAC 78, acquisition number of data points, which is the number of data points that a module acting as a sensor collects, and acquisition repeat interval, which is the number of times a module acting as a sensor repeats the test, as shown in box 228.

If the address sent at the beginning of the main program loop is not a broadcast address and not it is not an address of a particular module the program running in that module then awaits a further broadcast command or a command directed to its own node address, as shown by line 230 extending back to beginning of the main program loop 232. If the address sent at the beginning of the main program loop is an address of a particular module but the next byte sent is not a valid command byte as in decision box 211, again the program running in that module returns along line 230 to the beginning of the main program loop 232 and awaits a further broadcast command or a command directed to its own node address.

Figure 8A:
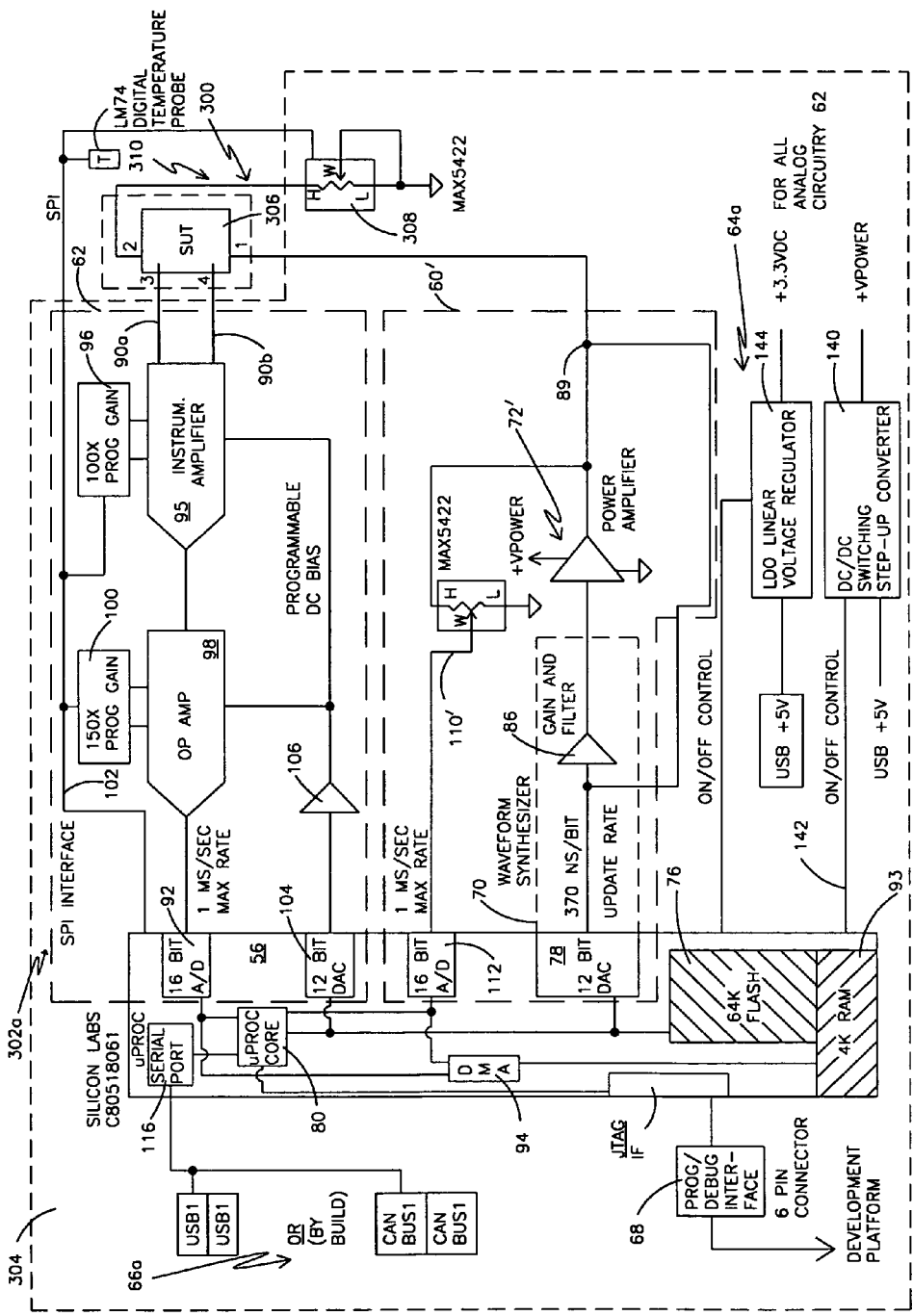
FIG. 8a is a block diagram of another embodiment of the miniaturized electronics with a wired connector, as shown in FIG. 4a, connected for providing stimulation for impedance monitoring in a voltage divider configuration.
Figure 8B:
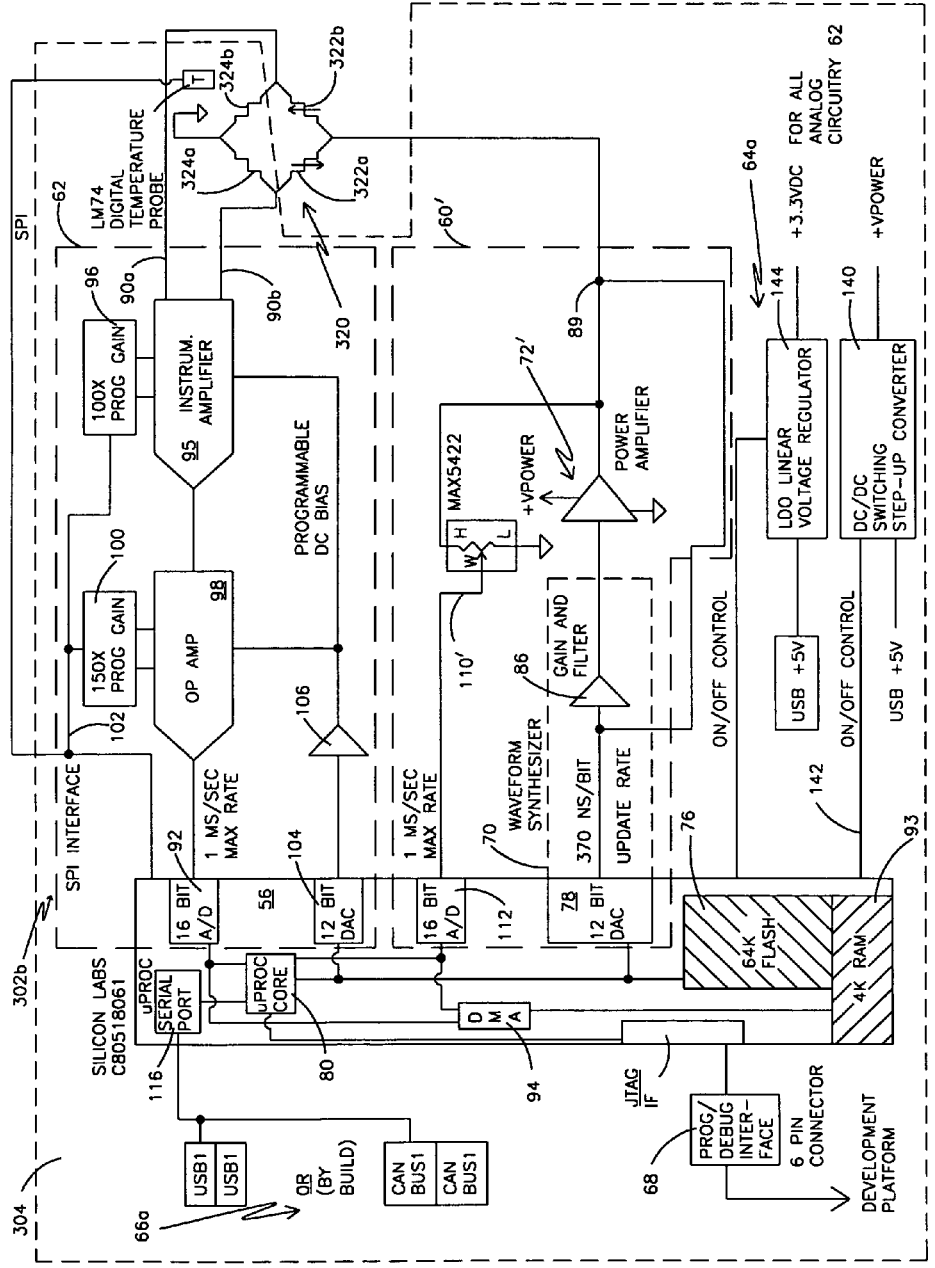
FIG. 8b is a block diagram of another embodiment of the miniaturized electronics with a wired connector connected for providing stimulation for impedance monitoring in a bridge configuration.
Figure 8C:
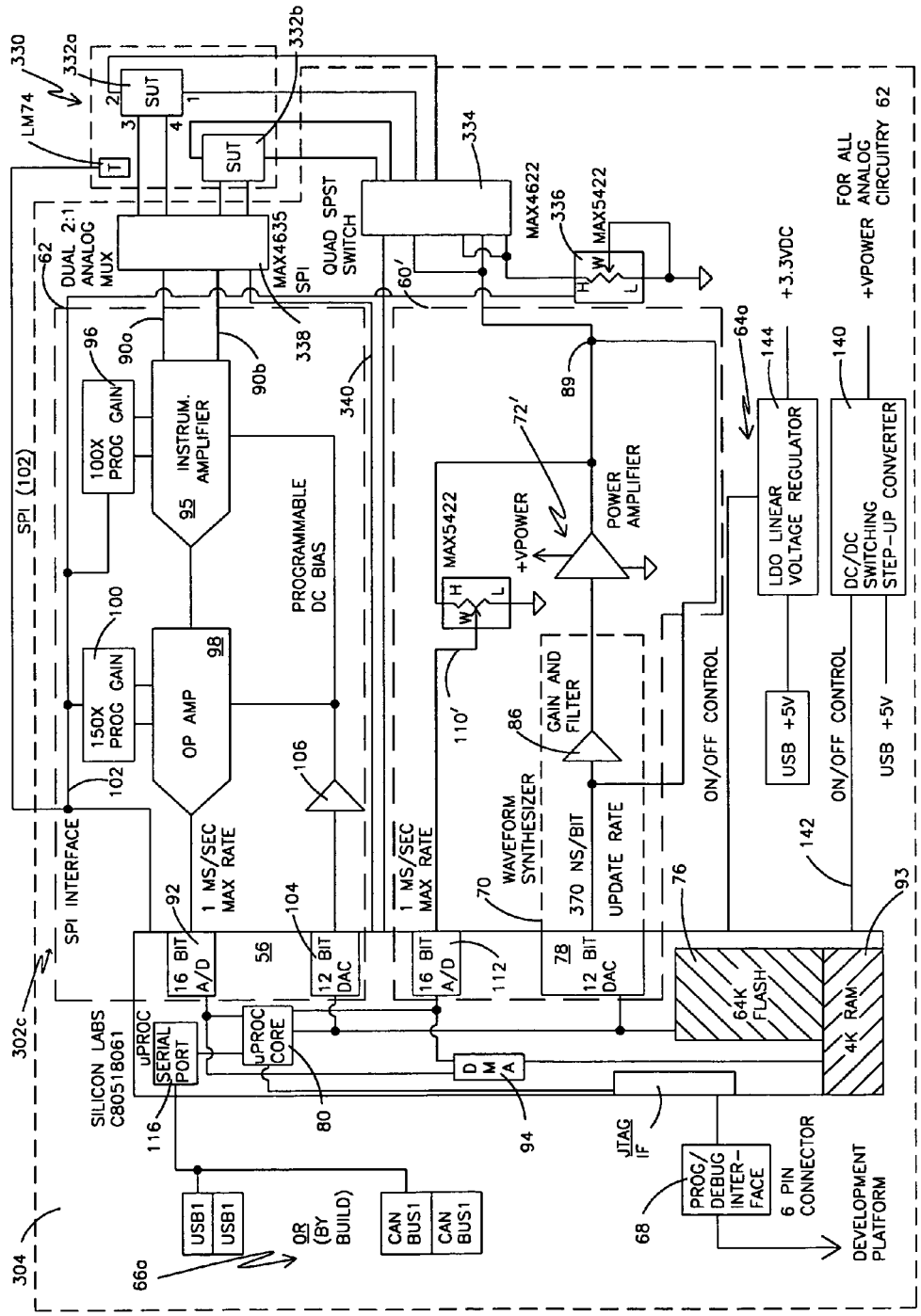
FIG. 8c is a block diagram of another embodiment of the miniaturized electronics with a wired connector connected for providing stimulation for impedance monitoring to a network of devices under test in a voltage divider configuration.

In another embodiment, the module is mounted on a material or on a structure. For example, it may be embedded within concrete of a roadway. The module includes a test device and a miniaturized source of stimulation. The test device can be a capacitor, an inductor, a resistor, or one or more electrodes for providing the electrical stimulation to the material or structure, as shown in FIGS. 8a-8c. The electrical stimulation from the miniaturized source of stimulation can be a desired waveform stored in memory or it can be a scan over a range of frequencies. The test device may be used to provide electrical impedance data about the material or structure.

The miniaturized source of stimulation can be programmable electrical signal generator 60, as described herein above and illustrated in FIGS. 4a-4e. In one embodiment, fixed push pull transistors 88 can be used for power amplifier 72, as shown in FIGS. 4a-4d. Other fixed power amplifiers can also be used, as is well known in the art.

Alternatively the miniaturized source of stimulation can be programmable electrical signal generator 60', as shown in FIGS. 8a-8c that includes programmable power amplifier 72'. Programmable power amplifier 72' can provide a waveform having an amplitude under control of a program running on microprocessor core 80.

One way to provide programmable power amplifier 72' is to provide a variable source of power at +V pin of a fixed power amplifier, thereby providing a way to adjust the amplitude of signal delivered by the fixed power amplifier and attain a gain controlled power amplifier. Another way is to provide a fixed source of power at +V pin of a programmable gain power amplifier.

Variable voltage divider 110' is used to provide an appropriate level of the loaded waveform back to 16 bit A/D converter 112 for recording.

Signal generator 60, 60' can include a programmable frequency synthesizer to provide a signal that interrogates the impedance at a desired fixed frequency, over a sweep of frequencies, or with a desired waveform to determine material properties. Spectral curves of impedance v. frequency, which provide material properties, can be obtained from a sweep of frequencies, as is well known in the art.

Microprocessor core 80 can also run a program to calculate the impedance and to provide electrical impedance spectroscopy analysis on the impedance v. frequency data. For example, the program can identify peaks in the impedance v. frequency curve. Thus, impedance spectroscopy analysis can be performed in microprocessor core 80 on or within the structure or material being analyzed. From the impedance spectroscopy data a measurement of the dielectric constant or permeability of the material under test can be determined. Whether a material, such as epoxy or concrete, has fully cured can be determined according to whether the measured impedance indicates that its dielectric constant is as high as expected.

Memory 76, 93 to log data, wireless communications link 66a, 66b, and power supply 64a, 64b, 64c, are also included in the module mounted on the material or structure, as described herein above and illustrated in FIGS. 3a-3b, 4a-4e, and FIGS. 8a-8c. USB 66a, shown in FIG. 8a can be replaced with wireless transmitter 66b, as shown in FIG. 4b. This wireless communications embodiment, with on-board signal generator 60, 60', data logging 62 and 78, 93, and on-board microprocessor 80 directing programmable devices and running data analysis software, allows very large numbers of modules to be mounted on a structure or embedded within a material, such as concrete, all operating independently and all capable of communicating their data without the need for long lead wires from each module.

Electronic impedance spectroscopy circuit 298 includes miniaturized electronics 302a and electrodes 1-4 on circuit board 304 along with front end 300 that includes SUT 306 and variable resistor 308, as shown in FIG. 8a. Electronic impedance spectroscopy circuit 300 includes test device 306 and variable resistor 308 in a voltage divider configuration. Variable resistor 308 can be, for example, MAX5422. Alternatively a bank of eight precision, low temperature coefficient resistors can be combined with a software controlled switch, such as the MAX4571, under the control of microcontroller 56 using an SPI interface to create programmable variable resistances. Variable resistor 308 is controlled by microprocessor 80 through the same SPI interface 102 used to control instrumentation amplifier 95 and programmable gain amplifier 98, as shown in FIG. 8a. Voltage divider 310 provides that only a fraction of the power delivered by power amplifier 72' is provided to instrumentation amplifier 95.

Alternatively a bridge configuration can be used, as shown in FIG. 8b. Bridge 320 includes impedance under test 322a, 322b along with fixed impedances 324a, 324b. For example, impedance under test 322a, 322b can be a coil or two coils with a moveable permeable or conductive core, such as a differential variable reluctance transducer (DVRT). Alternatively, three fixed impedances can be used with a device under test in bridge location 322a. A reference impedance, acting as a gold standard can be used in bridge location 322b. The reference impedance may have characteristics that closely match that of the test structure and whose aging characteristics reflect the aging expected of the test structure. Circuit board 304 can include fixed impedances 324a, 324b along with the rest of miniaturized electronics 302b.

Array of devices under test 330 can all be connected to single miniaturized electronics 302c on circuit board 304, as shown in FIG. 8c. An implementation for an array of two devices 332a, 332b is shown but this can be expanded to include a larger array, for example by including duplicate components or by including switches with more switching elements. A reference impedance, can be used as one of the devices in the array and the results for devices being tested can be compared with the reference impedance. While a voltage divider configuration is shown, a bridge configuration can also be used for each device under test, 332a, 332b.

In one embodiment, power amplifier 72' provides signal to one device at a time, either device under test 332a or 332b through MAX4622 quad single pole single throw switch 334. The return path, again through switch 334 and then through variable resistor 336, extends to ground. Variable resistor 336 can be a MAX5422. Signal from device under test 332a or 332b is received through dual 2:1 analog mux 338 by instrumentation amplifier 95 for amplification as described herein above in the description of FIGS. 4a-4e. A MAX4635 can be used for dual 2:1 analog mux 338. Switch 334 and switch 338 are both controlled by respective control lines 340 and 342 microcontroller 56.

As described herein above, test devices having interdigitizing fingers are commercially available to measure capacitance, and these test devices have been embedded in composite material and stimulated over a range of frequencies to measure impedance indicating the degree of cross linking in the composite material or in an epoxy, for example.

An approach described in a National Physical Laboratory (NPL) paper, "Good Practice Guide to Cure Monitoring," incorporated herein by reference, describes use of a sinusoidal voltage applied to a pair of electrodes embedded in a resin to stimulate a response current in the resin having a phase different from the applied voltage. Measuring properties of that response current provides another way to monitor conductance and capacitance of the resin during curing. The NPL paper describes how the electrodes may be arranged for dielectric measurements using inter-digitated electrodes, parallel plate electrodes, or coaxial electrodes and how they may be mounted as an integral part of a wall of a mold used for curing. Long lead wires were needed to connect such probes to a central signal stimulation and analysis device that was located away from the structure or material being tested.

U.S. Pat. No. 5,738,107 to Martinsen, incorporated herein by reference, illustrates another example of a system that provides a periodic electrical signal to measure a property of a material with electrodes mounted on the material. The Martinsen patent describes a system for measuring moisture content in skin by providing a periodic electrical signal in two concentric electrodes contacting the skin. Susceptance, the ac counterpart of conductance, which is related to the hydration of the stratum corneum layer of the skin, is measured using a third electrode contacting the skin. A measurement over a fixed frequency in the range from 1 to 50 khz is described. However, in Martinson only the electrodes appear to be mounted on the skin. There is no teaching of providing an on-board waveform synthesizer, on-board memory, an on-board device for supplying electrical power, or an on-board wireless communication link.

The present patent application provides a way to accomplish these and other tasks while eliminating lead wires by generating the waveform and providing the excitation and data acquisition right at the location of the module where the stimulation is applied and where the measurement is being made. The stored data may then be transmitted or the analysis done locally before transmission, as described herein above.

The material or structure can be measured while a chemical process is going on, such as curing of plastic or epoxy, setting of concrete, setting or deterioration of paint, ripening of fruit, changing moisture content of skin, or any other chemical reaction.

Lubricant in a motor can be measured during operation of the motor to monitor its degradation and determine the proper time for changing the oil. Dip stick 344 includes interdigitated capacitor 346 and piezoelectric transducer element 348, as shown in FIGS. 9a-9b. Printed circuit board 350 with the electronic components shown in FIGS. 8a-8c is provided in handle 352 with wiring extending through hollow dip stick 344 to connect printed circuit board 350 with capacitor 346 and piezoelectric transducer 348. Cap 354 protects piezoelectric transducer 348 during normal operation.

Figure 10B:
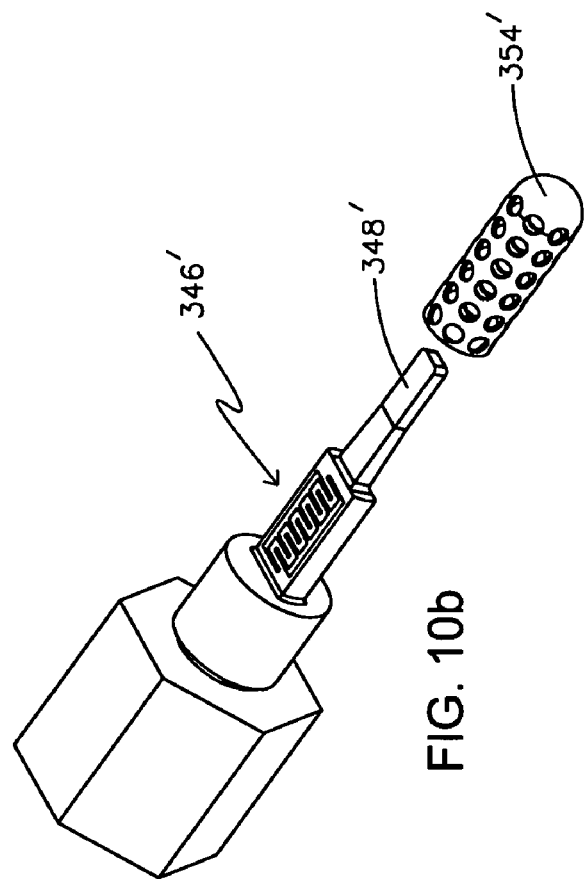
FIGS. 10a-10b are three dimensional diagrams of an oil pan plug for use in a vacuum pump or an internal combustion engine having miniaturized electronics, as shown in FIGS. 4a-4e and 8a-8c, in the nut portion and threaded portion and having impedance measuring and vibration delivering and sensing devices.
Figure 10A:
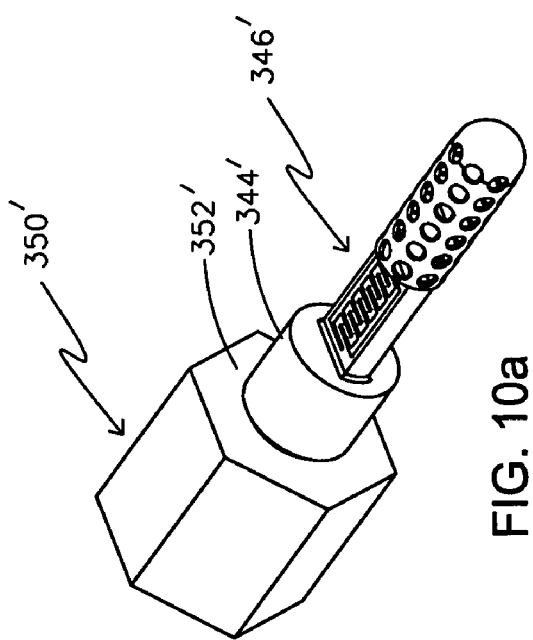

Alternatively, oil pan plug 360 includes interdigitated capacitor 346' and piezoelectric transducer element 348', as shown in FIGS. 10a-10b. Printed circuit board 350' with the electronic components shown in FIGS. 8a-8c is provided in plug 352' with wiring extending through hollow extendor 344' to connect printed circuit board 350' with capacitor 346' and piezoelectric transducer 348'. Cap 354' protects piezoelectric transducer 348' during normal operation. In either case inter-digitated capacitor 346, 346' can be used to determine the level of oil in the motor and feed back that information to the operator. The interdigitated capacitor can also be used to provide information about electrical properties of the oil that can indicate whether it is time for an oil change in an engine or vacuum pump.

The module with its capacitor having electrodes, such as inter-digitated electrodes or bar shaped electrodes, can be placed in the epoxy, concrete, reaction vessel, or motor. The reacting material or the oil serves as the dielectric between the electrodes. The on-board source of stimulation from signal generator 60' provides the signal. Measurements can be taken repeatedly while the reaction is going on. The data is recorded locally in flash 76 or RAM 93 and can be analyzed locally in microprocessor core 80. Changes in a material property can be detected as a result of changes in impedance or dielectric constant of the material between the plates of the electrodes as determined from the stimulation to the material and sensing of the response signal.

The module of the present patent application can also be included inside a pipe, such as a discharge pipe to monitor the material flowing in the pipe and to determine whether something different or unusual is flowing through the pipe, as determined by a change in impedance detected by the test structure. For example, a hydrocarbon has a very different impedance profile than water. Movement of a pollutant containing oil through a pipe ordinarily containing water could quickly be detected.

Similarly, a seal can be monitored to detect failure with a module that checks for moisture or another material that may penetrate through the seal.

Modules can also be used to detect a corrosive environment, for example by detecting moisture or corrosive chemicals in the environment.

Figure 11:
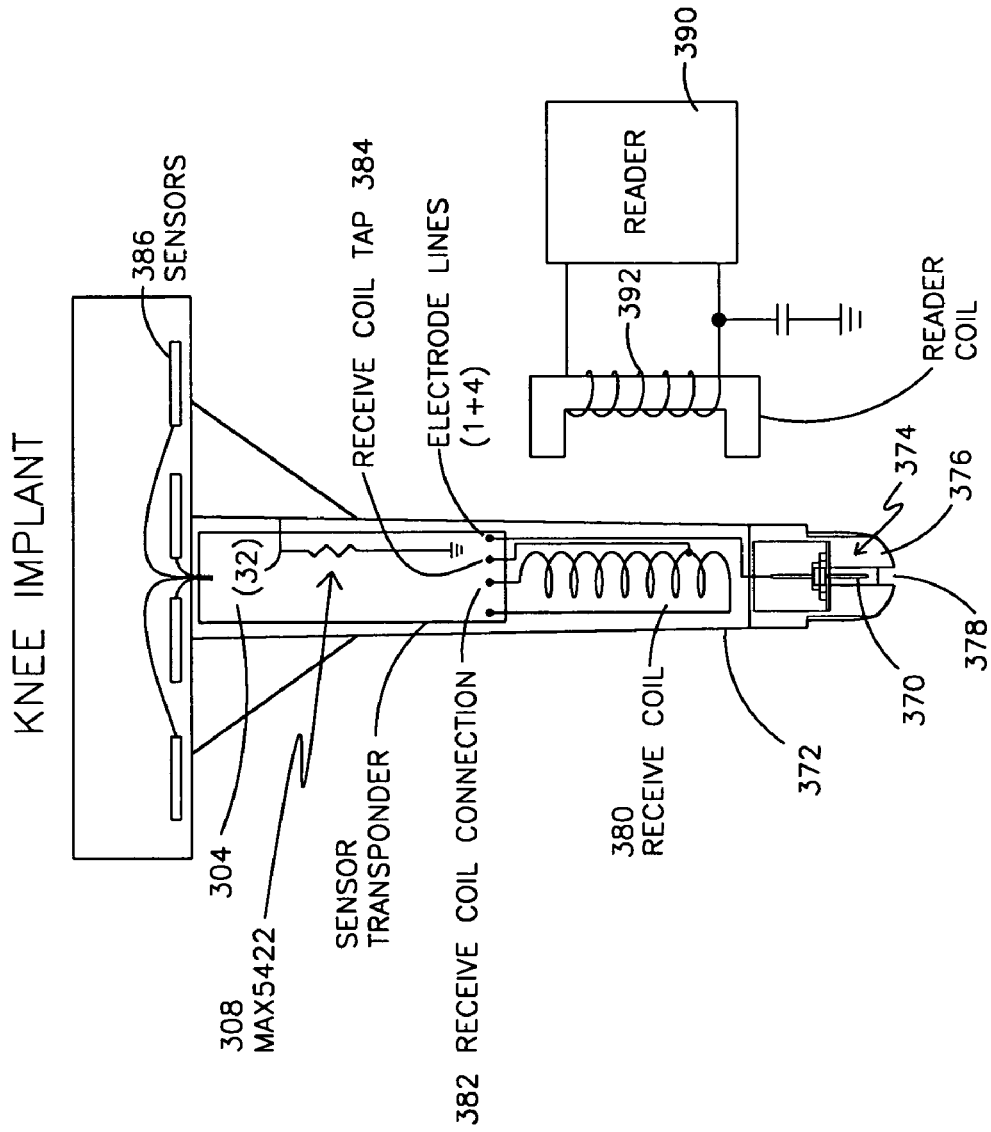
FIG. 11 is a schematic drawing of a knee implant showing an embodiment of the miniaturized electronics hermetically sealed in the implant case and with external electrodes for providing information about bone and tissue outside the implant in which power is supplied electromagnetically from a reader.

The apparatus of the present patent application also allows wirelessly measuring such things as tumor growth, bone growth or properties of a bone implant such as the interface between bone and implant, as shown in FIG. 11 for a knee implant, modified from commonly assigned US patent application 2004/0113790 ("the '790 application"), incorporated herein by reference. Ring electrodes, a patch of electrodes, or single wire electrode 370 can be used to test electrical impedances by sending an electrical waveform signal through the bone while other electrodes, such as metal implant case 372, detects that signal. Tissue, bone, and the interfacial structures there between can be analyzed from the received electrical signal. The module may be included within implant case 372, as described in the '790 application. Electrode 370 may be provided extending outside of implant case 372, wherein the electrode is electrically insulated from metal case of the implant by insulating feedthrough assembly 374.

Feedthrough assembly 374 includes a circumferential metal that can be welded to implant case 372 to create a hermetically sealed package. Metal implant case 372 is locally grounded to the ground plane of the printed circuit board located within implant case 372. Thus, metal implant case 372 provides the ground electrode. The electrode extending through feedthrough 374 is used to deliver complex waveforms to body tissues surrounding implant case 372 for electrical impedance spectroscopy of the body tissues, such as the interface between implant and bone. The location of electrode 370 can be changed from the position illustrated in FIG. 11 or multiple electrodes can be deployed. The embodiment shown in FIG. 11 requires only one feedthrough. This electrode is located at an end of the implant where mechanical stress is least to ensure that the feedthroughs' hermetic seals are not subject to mechanical fatigue. Protective cover 376 for electrode 370 is provided that has hole 378 along its center to allow access of body materials to electrode 370. Variable resistor 308 is provided in series between implant case 372 and ground, as shown in FIG. 8a. Contacts 1 and 4 from power amplifier 72' and from instrumentation amplifier 95 are tied together on circuit board 304 to extend to electrode 370 as a single wire. Contacts 2 and 3 from instrumentation amplifier 95 and from variable resistor 308 are also tied together on circuit board 304.

Implant case 372 in FIG. 11 also includes receive coil 380, its contacts 382 and its tap 384 on circuit board 304, and the electronic components illustrated in FIG. 8a on circuit board 304. Sensors 386 may also be included. Reader 390 with reader coil 392 provides radiation that is received by receive coil 380 for powering electronic circuits in the implant.

Electrode 370 can also be used as an RF antenna for communications external to implant case 372. In this dual use embodiment an electronically controlled antenna switch would be provided on board 55b of FIG. 4b. The antenna switch may be an electro-mechanical relay or a solid state semiconductor device.

In communications mode the antenna switch connects antenna electrode 370 to an RF circuit, such as transceiver 120 on board 55b, as shown in FIGS. 4b-4e. Alternatively, the RF circuit may be a transmitter or a receiver. The RF signal on the antenna electrode 370 is isolated from impedance spectroscopy circuit 300 by the amount of off-state isolation of the antenna switch.

For impedance spectroscopy, the RF circuit is disconnected from the antenna electrode and the impedance of the RF circuit is isolated from transceiver 120 by the amount of off-state isolation antenna switch can provide. In this mode the impedance spectroscopy circuit is connected to antenna electrode 370 and uses it as a probe for impedance spectroscopy measurements.

Figure 12A:
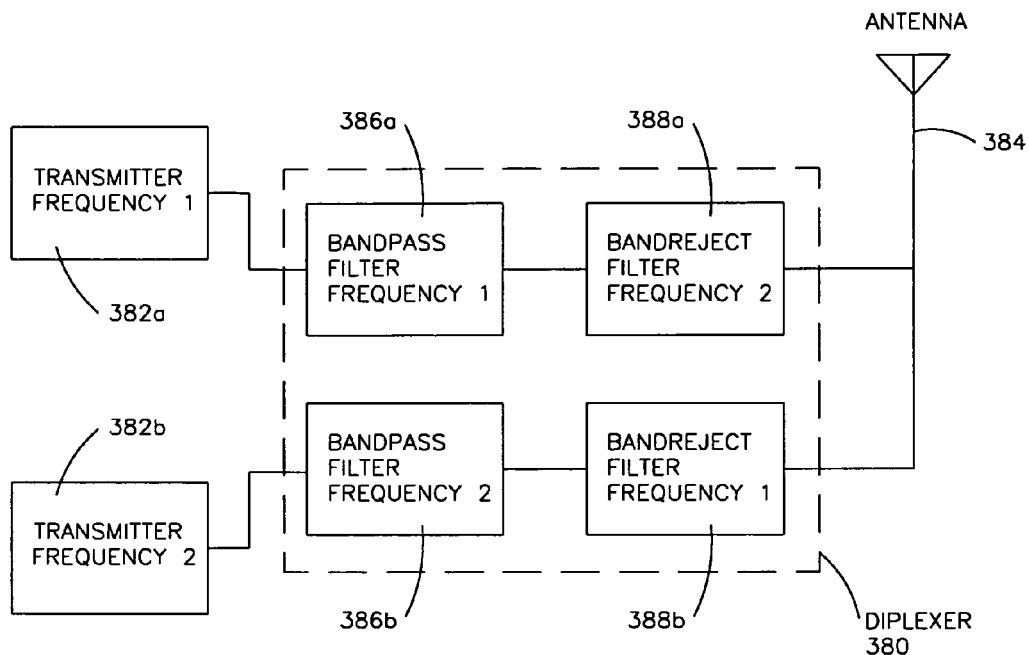
FIGS. 12a-12c are schematic diagrams of embodiments of the communications portion used for impedance spectroscopy.
Figure 12B:
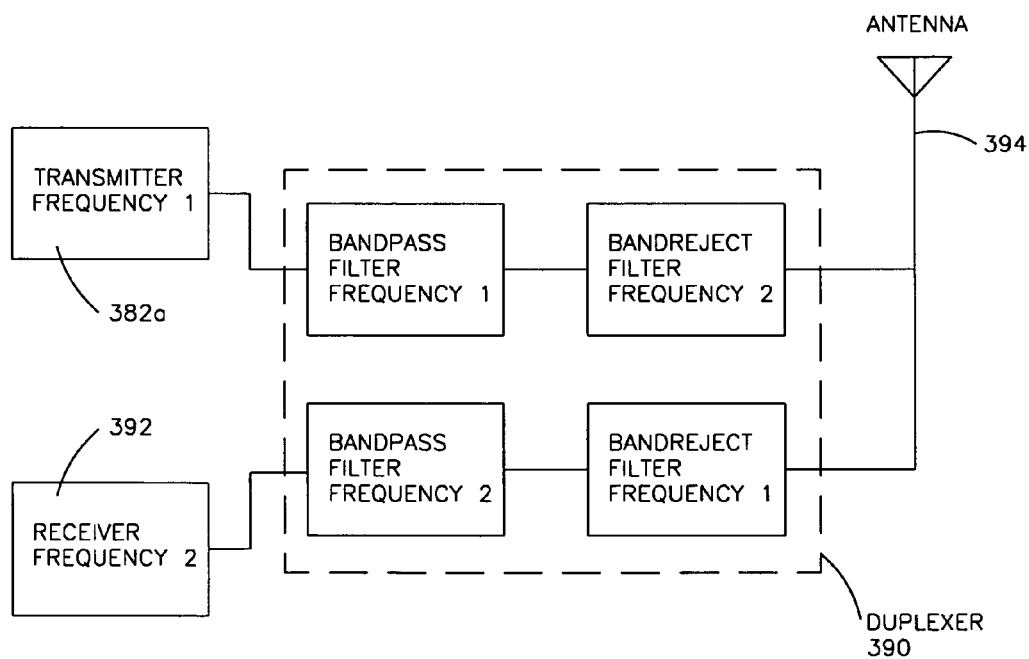

The frequencies used in impedance spectroscopy are typically very different from those used for RF communications. Diplexer 380 can be used instead of the switch, as shown in FIG. 12a to provide two transmitters 382a, 382b simultaneously transmitting signals from different sources (not shown) on the same antenna 384. Diplexer 380 includes bandpass filters 386a, 386b and bandreject filters 388a, 388b. Alternatively duplexer 390 can be used to provide simultaneous transmitting and receiving at different frequencies sharing one antenna, using transmitter 382a and receiver 392, as shown in FIG. 12b. Duplexer 390 has been used in older analog cordless telephones. Speaking into the handset provides a signal that is transmitted from handset antenna 384 back to the base set (not shown) on one frequency while voice from the other end of the conversation is transmitting from the base set to that same antenna 394 on the handset on a second frequency, as shown in FIG. 12b. Duplexer 390 allows one antenna to be used to allow both directions of communications simultaneously.

Figure 12C:
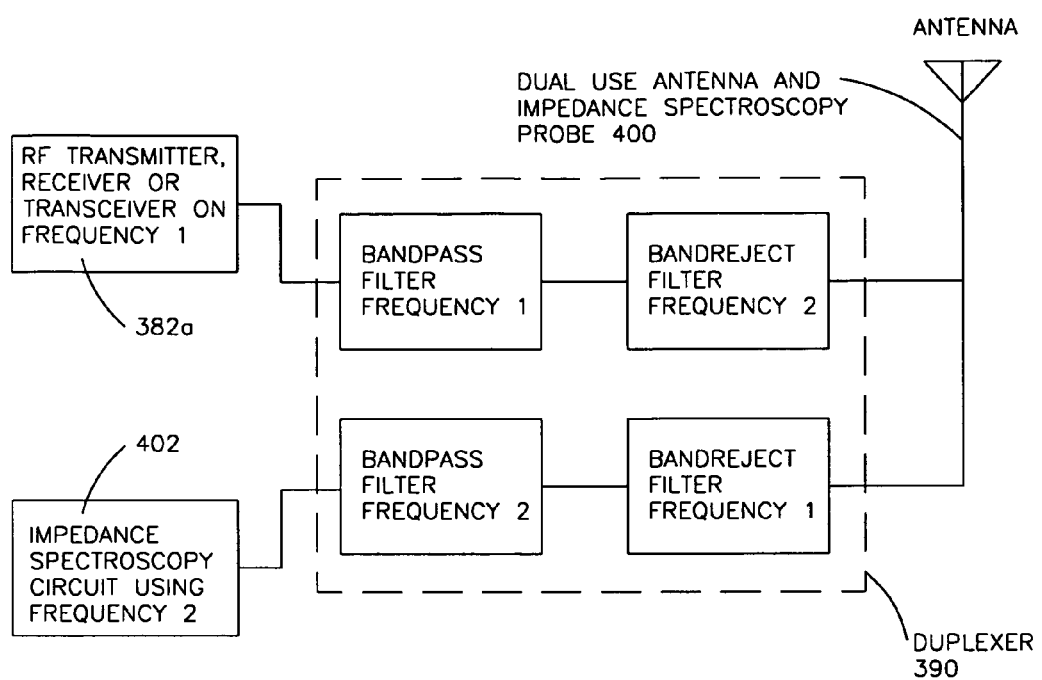

The present applicant found that a similar configuration using duplexer 390 allows transmission from antenna 400 from transmitter 382a while taking impedance spectroscopy measurements with impedance spectroscopy circuit 402, as shown in FIG. 12c. In this embodiment, impedance spectroscopy circuit 402 provides an RF signal which is swept over a range of frequencies and that signal is provided through filters of duplexer 390 to impedance spectroscopy probe 400. Loading of probe 400 by the material it contacts provides the magnitude and phase of impedance at each frequency which is reflected back through the filters of duplexer 390 and detected by impedance spectroscopy circuit 402. This spectroscopy data may be recorded or transmitted using RF transmitter 382a.

U.S. Pat. No. 5,441,527 ("the '527 patent"), incorporated herein by reference, shows an implantable bone growth stimulator for providing an AC or a DC current for electrically stimulating bone growth. The device includes circuits for monitoring parameters of the device itself, including battery charge, output voltage level but it does not provide a monitor of bone growth. FIG. 7 of the '527 patent shows a pair of electrodes contacting a healing bone growth mass adjacent a spine.

The present applicants recognized that their circuits could both provide a signal for stimulating growth of such a bone growth mass, when attached to electrodes, as described in the '527 patent. It could also perform impedance spectroscopy at the point of bone growth to monitor the rate of growth, to monitor chemistry, or to monitor mechanical properties of healing bone. The electrodes and associated electronics, as described herein above, could be provided within an implant case that can be implanted within the fusion site, or adjacent to it. For example, it could reside on or within portions of an implanted spinal fixation device or intervertebral "spacer" device.

In addition, the present applicants recognized that a piezoelectric element or several such piezoelectric elements could be included for acoustic impedance monitoring to measure mechanical properties of the healing bone, such as the mechanical acoustic impedance and/or acoustic transmissibility of healing bone, as well as properties of the bone/implant interface. The piezoelectric elements and associated microelectronics could be provided within an implant case that can be implanted within the fusion site, or adjacent to it, or could reside on or within portions of an implanted spinal fixation device or intervertebral "spacer" device. Changes in impedance of the piezoelectric elements and changes in the acoustic signals received either by reflection or by transmission from one piezoelectric device to another would be expected because the mechanical properties of the surrounding media (bone/tissue) change as healing progresses.

The '111 and the '444 patents show a needle shaped probe that can be used to monitor tissue impedance as a function of temperature, for example, to determine the location of a cancer and differentiate cancer tissue from non-cancer tissue. The '111 and '444 patents discuss measuring tissue electrical characteristics, such as electrical impedance, electrical conductance, electrical capacitance, dielectric constants; biochemical properties, such as measured by oxygen level, pH level, electrolytes concentration, and temperature; and structural properties, as measured by such techniques as ultrasound, acoustic impedance, electromagnetic potential, and light transmission. The probes of the '111 and '444 patents include provision for localized heating and cooling, for example, using the Peltier effect. The probes are particularly suitable for measuring impedance characteristics over a range of temperatures and the rate of change of impedance with temperature. However, both the 444 patent and the '111 patents require wired connection to external electrical current source, signal generators, and control circuits.

The present applicants recognized that a needle as described in the '111 and '444 patents, or a standard spinal needle, spinal pin, biopsy needle, or hypodermic syringe which has been instrumented with surface electrodes deposited or bonded on the external or internal surfaces of the pin or needle and that contains the power, control, and communications electronics described herein above and illustrated in FIGS. 4a-4e and FIGS. 8a-8c, could be used to measure electrical properties, such as impedance, of soft and hard tissues within the body without the need for wired connection to external boxes. The measurement could be made as these tissues are penetrated or after penetration by the pin or needle, as described in the '111 and '444 patents.

In addition to information coming from the electrodes being very useful in properly placing those electrodes for the monitoring, such a self-contained device could also precisely deliver a treatment (such as drugs/medications/proteins) to a specific structure or organ of the body or to a specific tumor or site within a tumor or cyst. The self-contained instrumented impedance spectroscopy needle could also be used to identify the correct tissues for biopsy as the biopsy is being performed.

U.S. Pat. No. 6,882,879 ("the '879 patent"), incorporated herein by reference, shows an impedance spectroscopy system for monitoring ischemic mucosal damage in hollow viscous organs. The system comprises a sensor catheter and an impedance spectrometer for electrically driving the catheter to obtain a complex tissue impedance spectrum. Once the catheter is in place in one of a patient's hollow viscous organs, the impedance spectrometer obtains the complex impedance spectrum by causing two electrodes in the tip of the catheter to inject a current into the mucosal tissue at different frequencies, while two other electrodes measure the resulting voltages. A pattern recognition system is then used to analyze the complex impedance spectrum and to quantify the severity of the mucosal injury. Alternatively, the complex impedance spectrum can be appropriately plotted against the spectrum of normal tissue, allowing for a visual comparison by trained personnel. However, while the probes are provided in the tissue, boxes with the signal generator and impedance spectroscopy support electronics are all provided outside the body, attached with wires passing through a catheter from those boxes to the organ of interest.

U.S. Pat. No. 6,813,515 ("the '515 patent"), incorporated herein by reference, shows using a coaxial probe wired to table top electronic boxes that records both the outgoing pulses from probes provided in the tissue and the reflected signal from a tip of a probe. 1-10 MHz frequency and the time of reflection depends on dielectric constant of material. However, boxes with the signal generator and impedance spectroscopy support electronics are all provided on a table top, attached with wires extending from those large boxes and through a catheter to the tissue of interest.

U.S. Pat. No. 6,337,994 ("the '994 patent"), incorporated herein by reference, shows an electrical impedance probe that includes a surgical needle. In an exemplary embodiment, the probe is a two-part trocar needle designed to acquire impedance measurements at its tip. The impedance measurements are representative of the local properties of a biological substance at the needle tip. Thus, the probe may be used to confirm needle insertion into a desired anatomical target or to identify the nature of the cells surrounding the tip of the needle. In urology, this sensor is used for confirming the needle insertion into the urinary tract, for localizing renal cell carcinoma, and prostate cancer. A separate impedance meter is used with the needle. The impedance meter is located separate from the needle and connected to the needle with wires, as shown in FIGS. 1, 2, 6, and 7.

In another embodiment, an array of electrodes can be connected to circuit board 304. Signal generator 60, 60' can be used to drive one of the electrodes with a complex waveform. Other electrodes can be used to receive the signal, as described herein above and illustrated in FIGS. 4a-4e, 8a-8c. For example, four probes can be used, two to provide the excitation signal and two for the measurement. The four probe arrangement allows use of high impedance measurement probes and avoids including IR drops from the applied current through wiring and contact resistance in the measurement. The number of electrodes can be reduced for an implant system to reduce complexity by combining as described herein above.

Impedance measurements of the test device may be made over the wide range of frequencies available from waveform synthesizer 70. Alternatively any desired stimulation waveform can be stored in memory 76, 93 and provided from power amplifier 72, 72', as shown in FIGS. 4a-4e, 8a-8c. Measurement data are recorded in memory 93, 76 and may be analyzed using on-board processor 80. Measurement data or data derived from the measurements may later transmitted to base station 135, 135'.

Because the waveform is generated and the data is stored on board 304, and because the device for supplying electrical power and the RF communications link are all on board 304, the need for wires extending from board 304 to base station 135, 135' is eliminated. The elimination of wiring makes large arrays of such devices on or embedded within the material or structure practical.

In addition to changes in material properties, the impedance changes may provide a measure of environmental influences such as changes in temperature, humidity, motion, or vibration. Changes in impedance can also be used to indicate a displacement or strain of a material. For example, physical motion or displacement of a permeable or conductive element located within or in close proximity to a coil can result in a change in impedance of the coil. This allows for a measurement of those motions, for example with a DVRT, which has a magnetically permeable or an electrically conductive core element. Physical movement of a structure to which it is attached will cause the core element to move, and that motion will change the impedance of the DVRT's coils. Those changes can be determined by providing a stimulation signal to the coils and measuring the changes in impedance.

Proximity to a substrate can also alter capacitance or inductance characteristics of an electrical signal, and those altered characteristics can be detected by capacitance or inductance sensors, such as DVRTs, connected to the signal generating and sensing electronics of the present patent application to give information about the substrate or changes in the substrate.

The Villari effect provides a change in magnetic permeability due to mechanical stress which may be detected by a change in inductance of a coil located near the material. Electrical impedance spectroscopy can be used to measure the change in impedance of that coil. The impedance represents both the resistive and reactive components. By exciting the coil with a complex waveform or with waveforms of different frequencies one can separate the coils responses to these waveforms in order to temperature compensate this measurement device, as described in commonly assigned U.S. Pat. Nos. 5,914,593, "Temperature Compensation Circuit," and 6,828,779, "Circuit for Compensating for Time Variation of Temperature in an Inductive Sensor," to Townsend and Arms, both of which are incorporated by reference, where DC and AC excitation were simultaneously used to measure a coil's reactance due to changes in inductance distinctly from a coils resistance which is dominated by temperature changes. The AC gives both the reactive and the resistive response while the DC only gives only the resistive response, so subtracting the two responses provides only the reactive response. The circuits provided herein in FIGS. 4a-4e and 8a-8c can provide such AC and DC waveforms and the response of the device to those waveforms allows one to separate reactive from resistive components and provide temperature compensation.

The excitation for the DVRT, as shown in FIG. 8b can include one frequency or it can include several frequencies. An arbitrary wave form can be provided as described herein above by uploading a lookup table to an on-board memory. A formula stored in memory can be used to generate the lookup table in a processor and then the wave form can be generated from the lookup table. Additional data points can be obtained by the processor providing interpolation between points. DC and AC waveforms or a combination can be used.

Either a differential technique, as shown in FIG. 8b or an impedance divider technique can be used, as shown in FIGS. 8a, 8c. The differential amplifier allows measuring the displacement as a function of the imbalance in the bridge caused by the change in impedance. The differential measurement of FIG. 8b removes variation from different environmental conditions, such as changes in temperature and humidity, since both sides of the bridge experience the same variation. As an alternative to a variable resistor, such as MAX 5422, a precision resistor can be provided, or a bank of resistors can be provided, such as MAX 3234.

To take advantage of this capability of varying stimulation frequency, the present inventors have provided a versatile wave form generator and signal conditioner able to provide a wide range of test devices with stimulation at a wide range of frequencies and collect data from each of them. Thus, with one such versatile wave form generator and signal conditioner circuit a wide range of test devices can be provided with stimulation. The test devices can be selected to best measure the properties of a specific material or structure, the drive frequency can be determined based on that specific test device, and the electronics can provide that drive frequency and analyze the data.

An AD 5934 chip or equivalent provides an alternate scheme to provide a fixed or variable frequency sine wave signal. The AD 5934 can provide a single frequency or it can sweep over a limited range of frequencies. However, the techniques of the present patent application provide the ability to provide and use a complex wave form that can contain a wide range of frequencies all at once. It can also include electronics to store a waveform lookup table. It can also include electronics that permits handling multiple sensors and actuators. It can also provide electronic drive circuitry for operating piezoelectric devices.

While the disclosed methods and systems have been shown and described in connection with illustrated embodiments, various changes may be made therein without departing from the spirit and scope of the invention as defined in the appended claims.

The invention claimed is:

1. An electronic system for testing a material, the system comprising:
 at least one module for mechanically mounting to the material, said at least one module including:
  a signal generator for generating a signal generator signal;
  a stimulus signal delivering device (SSDD) and an SSDD circuit for providing a device signal to the material wherein said device signal is derived from said signal generator signal, and wherein said device signal provided to the material includes a first type of energy, wherein interaction of said device signal with said material produces an interaction signal, wherein said interaction signal includes said first type of energy; and
  a sensor and a sensor circuit for receiving said interaction signal, wherein said sensor is sensitive to said first type of energy.

2. An electronic system as recited in claim 1, wherein said signal generator is programmable.

3. An electronic system as recited in claim 2, wherein said signal generator signal includes a multifrequency waveform having a waveform shape including multiple frequencies.

4. An electronic system as recited in claim 2, wherein at least one from the group consisting of waveform shape, duration of signals, number of signals provided, and timing of signals provided by said signal generator is programmable.

5. An electronic system as recited in claim 2, wherein said programmable signal generator includes a microprocessor programmable to provide a desired stimulus signal.

6. An electronic system as recited in claim 5, wherein said programmable signal generator includes a memory device for storing digital signal levels.

7. An electronic system as recited in claim 6, wherein said memory device is capable of storing a plurality of digitized data sets of digital signal levels.

8. An electronic system as recited in claim 7, wherein said microprocessor is capable of selecting from said digitized data sets of digital signal levels under program control to provide said signal generator signal.

9. An electronic system as recited in claim 2, wherein said programmable signal generator includes a digital to analog converter for providing said digital signal levels as an analog signal.

10. An electronic system as recited in claim 1, wherein said SSDD includes at least one from the group consisting of an actuator, a capacitor, an inductor, a resistor, and an electrode.

11. An electronic system as recited in claim 10, wherein said capacitor includes the material as a capacitor dielectric.

12. An electronic system as recited in claim 10, wherein said actuator includes a piezoelectric transducer.

13. An electronic system as recited in claim 1, wherein said at least one module further comprises a recording device for recording said interaction signal.

14. An electronic system as recited in claim 13, wherein said recording device is programmable.

15. An electronic system as recited in claim 14, wherein at least one of gain, offset, time data is collected, number of points collected, and acquisition rate by said recording device is programmable.

16. An electronic system as recited in claim 1, wherein said at least one module further comprises a microprocessor for analyzing said received signal to determine a property of the material.

17. An electronic system as recited in claim 16, wherein said microprocessor is capable of directing sampling data at a frequency of 1 Hz or higher.

18. An electronic system as recited in claim 17, wherein said data sampling frequency is programmable.

19. An electronic system as recited in claim 1, wherein said SSDD and said sensor are included in a single physical device.

20. An electronic system as recited in claim 19, wherein said single physical device is connected to said SSDD circuit and to said sensor circuit.

21. An electronic system as recited in claim 20, wherein said single physical device is connected to said SSDD circuit at a first time and to said sensor circuit at a second time different from said first time.

22. An electronic system as recited in claim 19, further comprising a plurality of said single physical devices all connected to a single SSDD circuit and to a single sensor circuit.

23. An electronic system as recited in claim 19, wherein single physical device includes at least one from the group consisting of a piezo device, a capacitor, an inductor, a resistor, and an electrode.

24. An electronic system as recited in claim 1, wherein said sensor circuit includes an a/d converter linked to said sensor to provide said received signal as digital data.

25. An electronic system as recited in claim 24, wherein said at least one module further comprises a signal conditioning, wherein said sensor provides said received signal to said signal conditioning, said signal conditioning including an amplifier for amplifying said received signal for providing to said a/d converter.

26. An electronic system as recited in claim 24, wherein said at least one module further comprises a first data storage device linked to said a/d converter, said first data storage device for storing said digital data.

27. An electronic system as recited in claim 26, wherein said first data storage device includes at least one from the group consisting of DRAM, SRAM, and NVRAM.

28. An electronic system as recited in claim 1, wherein said at least one module further comprises a communications link.

29. An electronic system as recited in claim 28, wherein said communications link is for transmitting data derived from said received signal.

30. An electronic system as recited in claim 28, wherein said communications link is for transmitting at least one from the group consisting of status and settings information and configuration parameters.

31. An electronic system as recited in claim 28, wherein said communications link is for receiving at least one from the group consisting of data, programs, and commands.

32. An electronic system as recited in claim 28, wherein said communications link includes at least one from the group consisting of a USB and a wireless link.

33. An electronic system as recited in claim 32, wherein said wireless link includes a data transceiver.

34. An electronic system as recited in claim 1, wherein said at least one module further comprises a microprocessor and a high voltage conversion electronics, said high voltage conversion electronics connected between said microprocessor and said SSDD, wherein said microprocessor controls output of said SSDD by providing a control signal to said high voltage conversion electronics.

35. An electronic system as recited in claim 1, wherein said signal generator is programmable, wherein said at least one module further comprises a first energy storage device, a digital recording device, and a communications link, said first energy storage device connected to provide power to run said programmable signal generator, said digital recording device, and said communications link.

36. An electronic system as recited in claim 35, wherein said first energy storage device includes a thin film battery.

37. An electronic system as recited in claim 35, wherein said at least one module further comprises a second energy storage device, said second energy storage device connected to provide a high current pulse.

38. An electronic system as recited in claim 35, wherein said at least one module further comprises a wireless battery charger connected to receive energy to recharge said first energy storage device.

39. An electronic system as recited in claim 38, wherein said wireless battery charger is coupled to receive power inductively.

40. An electronic system as recited in claim 38, wherein said wireless battery charger is coupled to receive power from apparatus for harvesting energy from its environment.

41. An electronic system as recited in claim 40, wherein said apparatus for harvesting energy from the environment converts at least one from the group consisting of light, vibration, and mechanical movement to electricity.

42. An electronic system as recited in claim 1, wherein said at least one module further comprises apparatus for harvesting energy from its environment wherein all energy for powering said signal generator, said SSDD and said circuit for receiving an interaction signal derived from interaction of said device signal with the material is derived from said energy harvesting apparatus.

43. An electronic system as recited in claim 1, further comprising a plurality of said modules linked in a network.

44. An electronic system as recited in claim 43, wherein said plurality of said modules are wired together.

45. An electronic system as recited in claim 43, wherein each said module of said plurality of modules has an address.

46. An electronic system as recited in claim 43, further comprising a reader, wherein said plurality of said modules are wirelessly linked to said reader.

47. An electronic system as recited in claim 43, wherein one of said modules can receive a command from another of said modules.

48. An electronic system as recited in claim 1, wherein said at least one module is capable of being mechanically mounted to the material so as to operate without interfering with normal use of the material.

49. An electronic system as recited in claim 1, wherein said first type of energy consists of acoustic energy.

50. An electronic system as recited in claim 49, wherein said SSDD includes a piezoelectric transducer, wherein said piezoelectric transducer converts said signal generator signal into said acoustic energy.

51. An electronic system as recited in claim 50, wherein said sensor includes a sensor piezoelectric transducer, wherein said sensor piezoelectric transducer converts said acoustic energy into an electrical signal.

52. An electronic system as recited in claim 1, wherein said first type of energy consists of electrical energy.

53. An electronic system as recited in claim 52, wherein said sensor includes a device for measuring an electrical parameter.

54. An electronic system as recited in claim 53, wherein said sensor includes an electrical impedance measuring device.

55. An electronic system as recited in claim 54, wherein said sensor provides electrical impedance as a function of frequency.

56. A method of operating a structure, comprising:
  (a) mounting an stimulus signal delivering device (SSDD) and a sensor to a portion of the structure;
  (b) mounting a first electronic circuit to said portion for stimulating said SSDD to provide a device signal to said structure, wherein said device signal includes a first type of energy, wherein said sensor is sensitive to said first type of energy and wherein said sensor provides information based on sensing said first type of energy;
  (c) mounting a second electronic circuit to said structure for receiving said information from said sensor, wherein said second electronic circuit includes memory for storing said information; and
  (d) while operating the structure in normal operation using said first electronic circuit, said SSDD, said sensor, said information, and said second electronic circuit to determine a property of said portion.

57. A method as recited in claim 56, comprising permanently mounting said SSDD and permanently mounting said first electronic circuit.

58. A method as recited in claim 56, wherein said structure includes at least one from the group consisting of a car, a truck, an aircraft, a water craft, a building, a pipeline, a bridge, a road, a machine, a tool, a living organism, and a geologic formation.

59. An electronic system as recited in claim 56, wherein said first type of energy consists of acoustic energy.

60. An electronic system as recited in claim 59, wherein said SSDD includes a piezoelectric transducer, wherein said piezoelectric transducer converts said signal generator signal into said acoustic energy.

61. An electronic system as recited in claim 60, wherein said sensor includes a sensor piezoelectric transducer, wherein said sensor piezoelectric transducer converts said acoustic energy into an electrical signal.

62. An electronic system as recited in claim 56, wherein said first type of energy consists of electrical energy.

63. An electronic system as recited in claim 62, wherein said sensor includes a device for measuring an electrical parameter.

64. An electronic system as recited in claim 63, wherein said sensor includes an electrical impedance measuring device.

65. An electronic system as recited in claim 64, wherein said sensor provides electrical impedance as a function of frequency.

66. An electronic system for testing a material, the system comprising:
  a combining device having a first port, a second port, and an antenna port;
  a first RF signal source connected to said first port;
  an impedance spectroscopy circuit having a second RF signal source connected to said second port, wherein said second RF signal source provides an RF signal that varies over a range of frequencies; and
  a conductor coupled to the material and connected to said antenna port, wherein said conductor serves as both an antenna for RF communication and as a probe for impedance spectroscopy, wherein said conductor coupled to the material has an impedance at each frequency of said range of frequencies, wherein said impedance spectroscopy circuit is connected for detecting said impedance at each frequency of said range of frequencies, wherein said impedance spectroscopy circuit provides impedance data for determining a parameter of the material.

67. A method of operating a structure, comprising:
  (a) mounting a signal generator to the structure, said signal generator for generating a signal generator signal;
  (b) mounting a stimulus signal delivering device (SSDD) to the structure, said SSDD for providing a device signal to the structure wherein said device signal is derived from said signal generator signal, and wherein said device signal provided to the structure includes electromagnetic energy; and
  (c) mounting a circuit to the structure for receiving an interaction signal, wherein said interaction signal is derived from interaction of said device signal with the structure, wherein said circuit is sensitive to a signal from said structure wherein said signal from said structure includes electromagnetic energy.

68. An electronic system as recited in claim 66, wherein said second RF signal source is capable of sweeping over a range of frequencies.

69. An electronic system as recited in claim 68, wherein said first RF signal source is part of a transmitter, further comprising a receiver to provide two way communications.

70. An electronic system as recited in claim 68, wherein said impedance spectroscopy circuit includes an impedance measurement portion.

71. An electronic system as recited in claim 68, wherein said conductor is coupled to a material and is for measuring properties of the material.

72. An electronic system as recited in claim 68, wherein said material includes at least one from the group consisting of a bone, a material subject to curing, a composite material, and concrete.

73. An electronic system as recited in claim 68, wherein said second RF signal source is capable of providing a waveform including a range of frequencies.

74. An electronic system as recited in claim 68, wherein said impedance spectroscopy circuit detects both magnitude of impedance and phase of impedance at each said frequency, and wherein said impedance spectroscopy circuit is connected for at least one from the group consisting of recording and transmitting.

75. An electronic system as recited in claim 68, wherein said parameter of the material includes at least one from the group consisting of a property of the material, an environmental influence on the material, a displacement of the material, and a strain of the material.

76. An electronic system as recited in claim 68, wherein said combining device is a duplexer.

77. An electronic system as recited in claim 68, wherein said combining device is a diplexer.

* * * * *